(12) United States Patent
Zheng et al.

(10) Patent No.: US 7,914,908 B2
(45) Date of Patent: Mar. 29, 2011

(54) ORGANIC ELECTROLUMINESCENT DEVICE HAVING AN AZATRIPHENYLENE DERIVATIVE

(75) Inventors: Shiying Zheng, Mcungie, PA (US); Liang-Sheng Liao, Rochester, NY (US)

(73) Assignee: Global OLED Technology LLC, Wilmington, DE (US)

( * ) Notice: Subject to any disclaimer, the term of this patent is extended or adjusted under 35 U.S.C. 154(b) by 733 days.

(21) Appl. No.: 11/934,258

(22) Filed: Nov. 2, 2007

(65) Prior Publication Data

US 2009/0115316 A1    May 7, 2009

(51) Int. Cl.
*H01L 51/54* (2006.01)
*C07D 471/12* (2006.01)
*C08G 73/06* (2006.01)
*H01J 1/62* (2006.01)

(52) U.S. Cl. ........ 428/690; 428/917; 313/504; 313/506; 528/423; 546/64

(58) Field of Classification Search .................. None
See application file for complete search history.

(56) References Cited

U.S. PATENT DOCUMENTS

| | | |
|---|---|---|
| 3,172,862 A | 3/1965 | Gurnee et al. |
| 3,173,050 A | 3/1965 | Gurnee et al. |
| 3,710,167 A | 1/1973 | Dresner |
| 4,356,429 A | 10/1982 | Tang |
| 4,769,292 A | 9/1988 | Tang et al. |
| 5,393,614 A | 2/1995 | Nakada |
| 2004/0076853 A1* | 4/2004 | Jarikov .......... 428/690 |

OTHER PUBLICATIONS

Pabst et al., Tetrahedron Letters, (1998), 39(48), pp. 8825-8828.*
Wang et al., Polymers for Advanced Technologies, (1996), 7(8), pp. 723-725.*
Dresner, Double Injection Electroluminescence in Anthracene, RCA Review, vol. 30, pp. 322-334, 1969.
Tang et al, Electroluminescence of doped organic thin films, J. Applied Physics, vol. 65, pp. 3610-3616, 1999.

* cited by examiner

*Primary Examiner* — Dawn Garrett
(74) *Attorney, Agent, or Firm* — McKenna Long & Aldridge LLP

(57) ABSTRACT

Azatriphenylene derivatives and their use in the electron-transporting layer of an electroluminescent device that comprises an anode, a spaced-apart cathode, and at least one electron-transporting layer disposed between the spaced-apart anode and cathode. Such EL devices provide lower drive voltage, improved power efficiency, and longer operational lifetime.

11 Claims, 2 Drawing Sheets

ORGANIC ELECTROLUMINESCENT DEVICE HAVING AN AZATRIPHENYLENE DERIVATIVE

FIELD OF INVENTION

The present invention relates to the use of azatriphenylene materials in an electron-transporting layer in an organic EL device.

BACKGROUND OF THE INVENTION

Organic electroluminescent (EL) devices are electronic devices that emit light in response to an applied potential. The structure of an EL device comprises, in sequence, an anode, an organic EL medium, and a cathode. Although organic electroluminescent (EL) devices have been known for over two decades, their performance limitations have represented a barrier to many desirable applications. In simplest form, an organic EL device includes an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322-334, 1969; and Dresner U.S. Pat. No. 3,710,167, issued Jan. 9, 1973. The organic layers in these devices, are usually composed of a polycyclic aromatic hydrocarbon, that are very thick (much greater than 1 μm) and highly resistive. Consequently, operating voltages were very high, often >100V.

More recent organic EL devices include an organic EL element consisting of extremely thin layers (e.g. <1.0 μm) between the anode and the cathode. Herein, the term "organic EL element" encompasses the layers between the anode and cathode electrodes. Reducing the thickness lowered the resistance of the organic layer and has enabled devices that operate much lower voltage. In a basic two-layer EL device structure, described first in U.S. Pat. No. 4,356,429, one organic layer of the EL element adjacent to the anode is specifically chosen to transport holes, therefore, it is referred to as the hole-transporting layer, and the other organic layer is specifically chosen to transport electrons, referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al [*J. Applied Physics*, Vol. 65, Pages 3610-3616, 1989]. The light-emitting layer commonly consists of a host material doped with a guest material. Still further, there has been proposed in U.S. Pat. No. 4,769,292 a four-layer EL element including a hole-injecting layer (HIL), a hole-transporting layer (HTL), a light-emitting layer (LEL) and an electron-transporting/injecting layer (ETL). Still further, there are other multi-layer EL devices that contain additional functional layers, such as an electron-blocking layer (EBL), and/or a hole-blocking layer (HBL) in the devices. At the same time, numerous types of organic materials have been discovered and used in organic EL devices. These new structures and new materials have further resulted in improved device performance.

Besides the above organic EL devices including low molecular weight materials, an EL device wherein the EL element including a polymer such as poly(fluorene) derivative, poly(p-phenylenevinylene) derivative, and poly (thiophene) derivative, and a device including a mixture of a polymer such as poly(vinyl carbazole) with a low molecular weight light emitting material and an electron-transporting material have been developed.

Improving operational stability and lowering the required driving voltage is particularly important for the EL devices to be used in flat panel display. The inherent lack durability of organic materials used in the EL element of an EL device results in crystallization due to the heat evolved from the prolonged passage of current, and therefore shortened device lifetime. During device operation, if the temperature inside of a device (defined as device temperature) is higher than a glass transition temperature (Tg) of an organic layer in an EL device, the organic layer will change its film formation from an amorphous state to a polycrystalline formation. This change will not only cause a film morphology change, but also cause a possible change in its ionization potential (IP) or its electron energy band gap (Eg). As a result, electrical shorts can occur, carrier injection can deteriorate, or luminance efficiency can be reduced.

In particular, much effort has been directed to the discovery of useful electron-transporting materials. There are problems associated with many existing and commonly used electron-transporting materials such as undesired emitting color from electron-transporting material itself, high driving voltage, and poor device lifetime.

Tris(8-hydroxyquinoline)aluminum (Alq), one of the metal chelated oxinoid compounds, has been a commonly used electron-transporting material in OLEDs since Tang et al. disclosed its use in "Organic Electroluminescent Diodes", *Applied Physics Letters*, 51, 913 (1987). Alq has a reasonably high Tg (about 172° C.). This property facilitates the operational stability of the EL device at a device temperature up to its Tg. However, the electron mobility of Alq is not as effective as expected and so the driving voltage is high. In addition, there is undesired light emission from Alq when this material is located in an ETL in a blue OLED.

U.S. Pat. No. 5,393,614 disclose a specific phenanthroline derivative, 4,7-diphenyl-1,10-phenanthroline (Bphen), as an electron-transporting material. Due to its high electron mobility and suitable energy band structure, Bphen can efficiently transport electrons from the cathode into the LEL resulting in high luminous efficiency and low drive voltage. However, Bphen has a low Tg (about 60° C.), and a vacuum deposited amorphous Bphen layer in an EL device can be readily changed into a polycrystalline layer during operation, which results in a sudden drop in luminance and a sudden increase in drive voltage. Its operational lifetime is no longer than 20 hrs if the device is operated at 70° C., substantially minimizing the effectiveness of this material in an EL device

SUMMARY OF THE INVENTION

It is therefore an object of the present invention to provide stable azatriphenylene compounds useful as electron-transporting layer in a multi-layer electroluminescent device.

These objects are achieved by an organic compound comprising an azatriphenylene structure represented by the formula:

Formula I

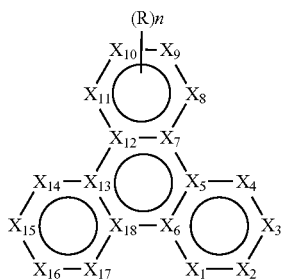

wherein

X1 to X18 are individually the same or different and where X5-X7, X12-X13 and X18 are all carbon and, where one of X1-X4 is a nitrogen, one of X8-X11 is a nitrogen and one of X14-X17 is a nitrogen;

R is a substituent independently selected from hydrogen, an alkyl group, a cycloalkyl group, a heterocyclic group, an alkenyl group, a cycloalkenyl group, an alkynyl group, a hydroxyl group, a mercapto group, an alkoxy group, an aryl group, a heteroaryl group, an amino group, a cyano group, a nitro group, an alkylthio group, an arylalkyl group, an aryl ether group, an aryl thioether group, a halogen, a haloalkane, a haloalkene, a haloalkyne, a silyl group, a siloxanyl group, an aldehyde group, a carbonyl group, a carboxyl group, an ester group, a carbamoyl group, a sulfonate group, a sulfinate group, an amide group, and a cyclic structure formed with an adjacent substitutent group; and n is integer of from 1 to 11 and when n is 2 or more the R substituents can form a fused ring structure.

The present invention makes use of an organic material in an electron-transporting layer in an EL device that provide improved results. These results can include improved thermal stability, efficiency, or lifetime of an EL device. The present invention can provide a highly efficient electroluminescent device with low driving voltage and long lifetime.

Figure 1:
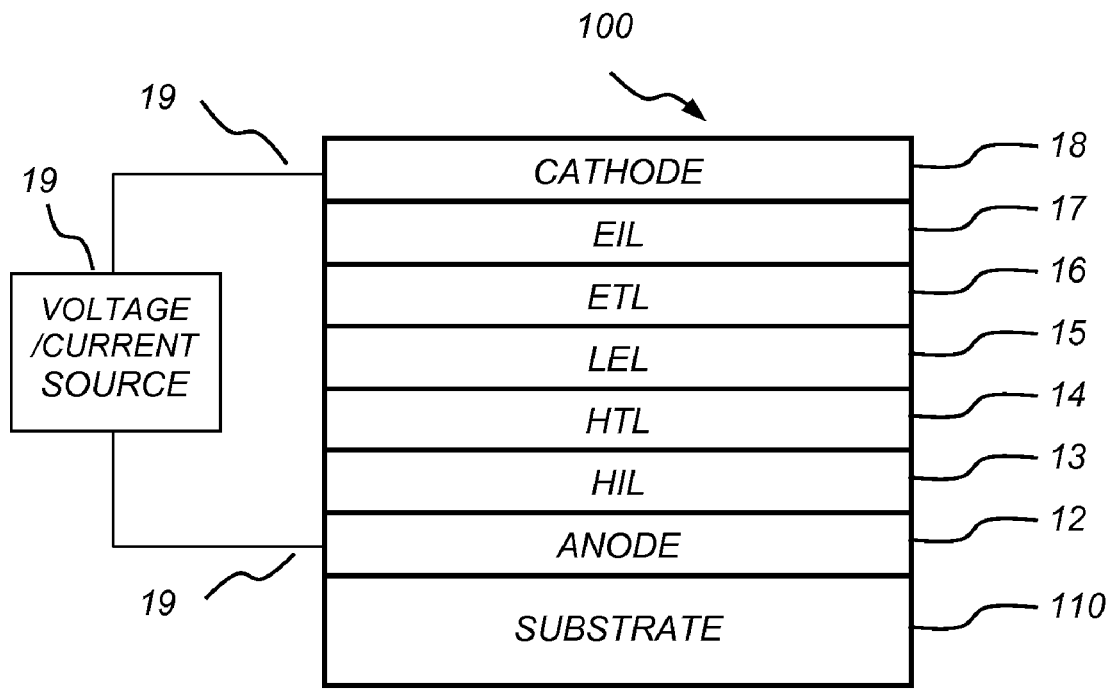
FIG. 1 shows a cross-sectional view of one embodiment of OLEDs in accordance with the present invention having an electron-transporting layer containing an azatriphenylene derivative.

Since device feature dimensions such as layer thicknesses are frequently in sub-micrometer ranges, the drawing of FIG. 1 is scaled for ease of visualization rather than dimensional accuracy.

DETAILED DESCRIPTION OF THE INVENTION

There is shown a cross-sectional view of one embodiment of an OLED in accordance with the present invention in FIG. 1. OLED 100 includes substrate 110, anode 120, HIL 130, HTL 140, LEL 150, ETL 160, EIL 170, and cathode 180. (HIL 130, HTL 140, LEL 150, ETL 160, and EIL 170 form an organic EL medium in between the anode 120 and cathode 180). OLED 100 is externally connected to a voltage/current source 192 through electrical conductors 191. OLED 100 is operated by applying an electric potential produced by the voltage/current source 192 between the pair of contact electrodes, anode 120 and cathode 180. Shown in FIG. 2 is OLED 200, which is the same as OLED 100 except that there are no HIL 130 and EIL 170 in OLED 200.

Figure 2:
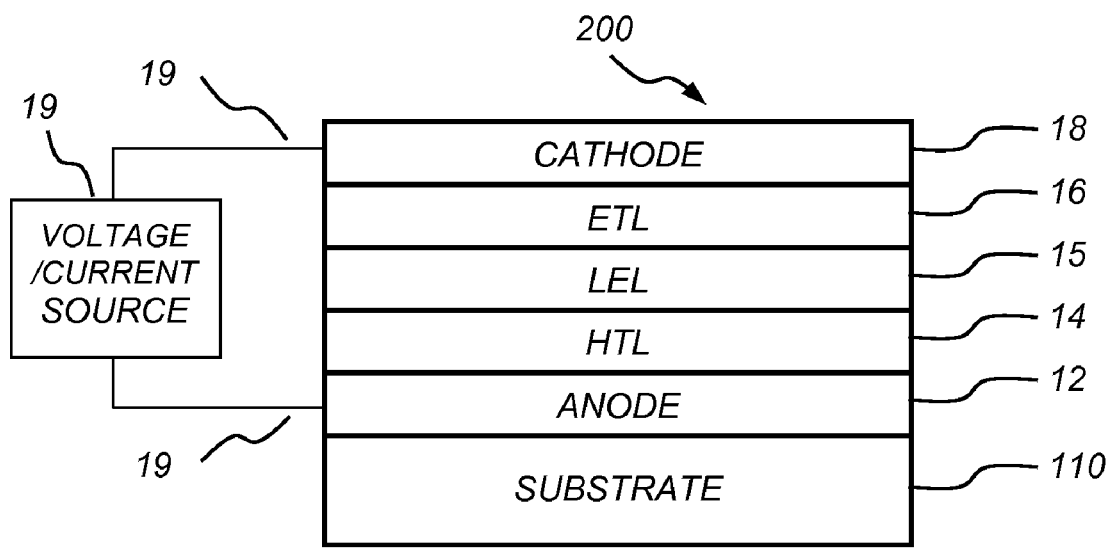
FIG. 2 shows a cross-sectional view of another embodiment of OLEDs in accordance with present invention having an electron-transporting layer containing an azatriphenylene derivative.

The following is the description of the device structure, material selection, and fabrication process for the OLED embodiments shown in FIGS. 1 and 2.

Substrate 110 is an organic solid, an inorganic solid, or include organic and inorganic solids that provides a supporting backplane to hold the OLED. Substrate 110 is rigid or flexible and is processed as separate individual pieces, such as sheets or wafers, or as a continuous roll. Typical substrate materials include glass, plastic, metal, ceramic, semiconductor, metal oxide, semiconductor oxide, or semiconductor nitride, or combinations thereof. Substrate 110 is a homogeneous mixture of materials, a composite of materials, or multiple layers of materials. Substrate 110 can also be a backplane containing TFT circuitry commonly used for preparing OLED display, e.g. an active-matrix low-temperature polysilicon TFT substrate. The substrate 110 can either be light transmissive or opaque, depending on the intended direction of light emission. The light transmissive property is desirable for viewing the EL emission through the substrate. Transparent glass or plastic are commonly employed in such cases. For applications where the EL emission is viewed through the top electrode, the transmissive characteristic of the bottom support is immaterial, and therefore is light transmissive, light absorbing or light reflective.

Anode 120 is formed over substrate 110 in FIGS. 1 and 2. When EL emission is viewed through the substrate 110, the anode should be transparent or substantially transparent to the emission of interest. For applications where EL emission is viewed through the top electrode, the transmissive characteristics of the anode material are immaterial and any conducting or semiconducting material is used, regardless if it is transparent, opaque or reflective. Desired anode materials are deposited by any suitable way such as thermal evaporation, sputtering, chemical vapor deposition, or electrochemical process. Anode materials are patterned using well known photolithographic processes.

The material used to form anode 120 is selected from inorganic materials, or organic materials, or combination thereof. The anode 120 can contain the element material selected from aluminum, silver, gold, copper, zinc, indium, tin, titanium, zirconium, hafnium, niobium, tantalum, molybdenum, tungsten, manganese, iron, ruthenium, rhodium, iridium, nickel, palladium, platinum, silicon, or germanium, or combinations thereof. The anode 120 can also contain a compound material, such as a conducting or semiconducting compound. The conducting or semiconducting compound is selected from the oxides of titanium, zirconium, hafnium, niobium, tantalum, molybdenum, tungsten, manganese, iron, ruthenium, rhodium, iridium, nickel, palladium, platinum, copper, zinc, indium, tin, silicon, or germanium, or combinations thereof. The conducting or semiconducting compound is selected from the sulfides of titanium, zirconium, hafnium, niobium, tantalum, molybdenum, tungsten, manganese, iron, ruthenium, rhodium, iridium, nickel, palladium, platinum, copper, zinc, indium, tin, silicon, or germanium, or combinations thereof. The conducting or semiconducting compound is selected from the selenides of titanium, zirconium, hafnium, niobium, tantalum, molybdenum, tungsten, manganese, iron, ruthenium, rhodium, iridium, nickel, palladium, platinum, copper, zinc, indium, tin, silicon, or germanium, or combinations thereof. The conducting or semiconducting compound is selected from the tellurides of titanium, zirconium, hafnium, niobium, tantalum, molybdenum, tungsten, manganese, iron, ruthenium, rhodium, iridium, nickel, palladium, platinum, copper, zinc, indium, tin, silicon, or germanium, or combinations thereof. The conducting or semiconducting compound is selected from the nitrides of titanium, zirconium, hafnium, niobium, tantalum, molybdenum, tungsten, manganese, iron, ruthenium, rhodium, iridium, nickel, palladium, platinum, copper, zinc, indium, tin, silicon, or germanium, or combinations thereof. Preferably, the conducting or semiconducting compound is selected from indium-tin oxide, tin oxide, aluminum-doped zinc oxide, indium-doped zinc oxide, magnesium-indium oxide, nickel-tungsten oxide, zinc sulfide, zinc selenide, or gallium nitride, or the combination thereof.

Although it is not always necessary, it is often useful to provide an HIL in the organic EL unit. HIL 130 can serve to facilitate hole injection from the anode into the HTL, thereby reducing the drive voltage of the OLED. Suitable materials for use in HIL 130 include, but are not limited to, porphyrinic compounds as described in U.S. Pat. No. 4,720,432 and some aromatic amines, for example, 4,4',4"-tris[(3-ethylphenyl)phenylamino]triphenylamine (m-TDATA). Alternative hole-injecting materials reportedly useful in organic EL devices are described in EP 0 891 121 A1 and EP 1 029 909 A1. Aromatic tertiary amines discussed below can also be useful as hole-injecting materials. Other useful hole-injecting materials such as dipyrazino[2,3-f:2',3'-h]quinoxalinehexacarbonitrile are described in U.S. Patent Application Publication No. 2004/0113547 A1 and U.S. Pat. No. 6,720,573.

Illustrative examples of useful hole-injecting materials include, but are not limited to, the following:

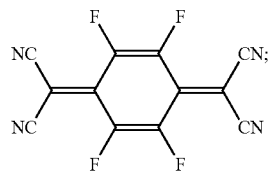

P-1

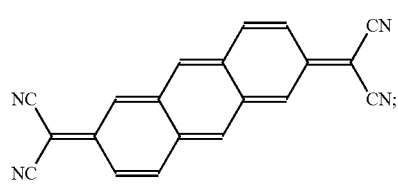

P-2

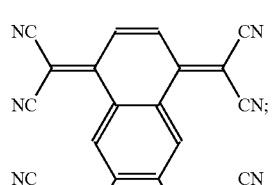

P-3

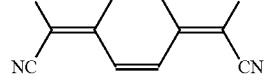

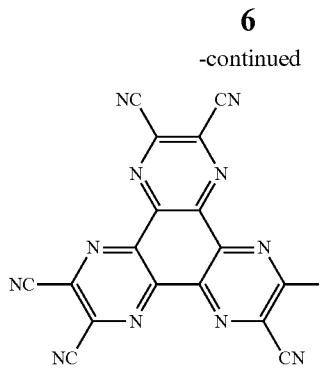

P-4

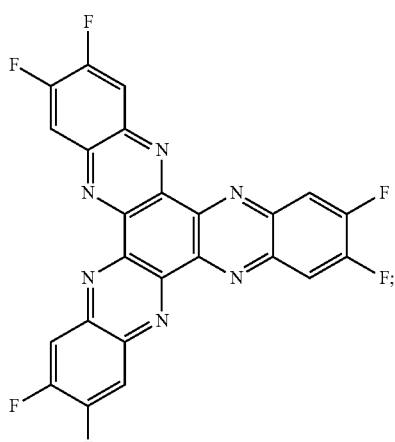

P-5

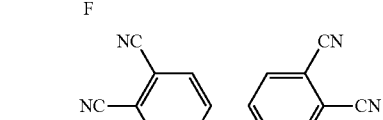

P-6

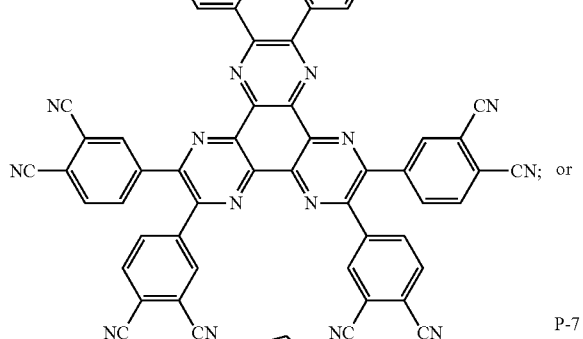

; or

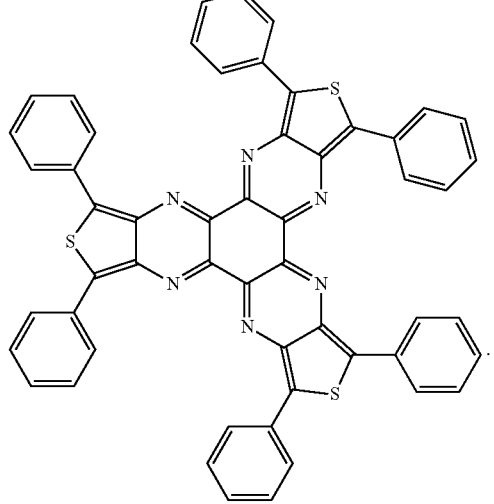

P-7

In addition, a p-type doped organic layer is also useful for the HIL as described in U.S. Pat. No. 6,423,429. The term "p-type doped organic layer" means that this layer has semiconducting properties after doping, and the electrical current through this layer is substantially carried by the holes. The conductivity is provided by the formation of a charge-transfer complex as a result of hole transfer from the dopant to the host material. The thickness of the HIL 130 is in the range of from 0.1 nm to 200 nm, preferably, in the range of from 0.5 nm to 150 nm.

The HTL 140 contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine is an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals or at least one active hydrogen-containing group are disclosed by Brantley, et al. in U.S. Pat. No. 3,567,450 and U.S. Pat. No. 3,658,520.

A more preferred class of aromatic tertiary amines are those which include at least two aromatic tertiary amine moieties as described in U.S. Pat. No. 4,720,432 and U.S. Pat. No. 5,061,569. Such compounds include those represented by structural Formula A

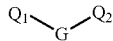

wherein:

$Q_1$ and $Q_2$ are independently selected aromatic tertiary amine moieties; and G is a linking group such as an arylene, cycloalkylene, or alkylene group of a carbon to carbon bond.

In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural Formula A and containing two triarylamine moieties is represented by structural Formula B

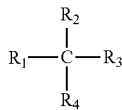

wherein:

$R_1$ and $R_2$ each independently represents a hydrogen atom, an aryl group, or an alkyl group or $R_1$ and $R_2$ together represent the atoms completing a cycloalkyl group; and $R_3$ and $R_4$ each independently represents an aryl group, which is in turn substituted with a diaryl substituted amino group, as indicated by structural Formula C

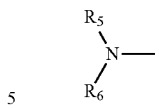

wherein $R_5$ and $R_6$ are independently selected aryl groups. In one embodiment, at least one of $R_5$ or $R_6$ contains a polycyclic fused ring structure, e.g., a naphthalene.

Another class of aromatic tertiary amines are the tetraaryldiamines. Desirable tetraaryldiamines include two diarylamino groups, such as indicated by Formula C, linked through an arylene group. Useful tetraaryldiamines include those represented by Formula D

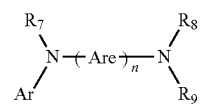

wherein:

each Are is an independently selected arylene group, such as a phenylene or anthracene moiety;

n is an integer of from 1 to 4; and

Ar, $R_7$, $R_8$, and $R_9$ are independently selected aryl groups. In a typical embodiment, at least one of Ar, $R_7$, $R_8$, and $R_9$ is a polycyclic fused ring structure, e.g., a naphthalene.

The various alkyl, alkylene, aryl, and arylene moieties of the foregoing structural Formulae A, B, C, and D can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, e.g. cyclopentyl, cyclohexyl, and cycloheptyl ring structures. The aryl and arylene moieties are typically phenyl and phenylene moieties.

The HTL is formed of a single or a mixture of aromatic tertiary amine compounds. Specifically, one can employ a triarylamine, such as a triarylamine satisfying the Formula B, in combination with a tetraaryldiamine, such as indicated by Formula D. When a triarylamine is employed in combination with a tetraaryldiamine, the latter is positioned as a layer interposed between the triarylamine and the electron injecting and transporting layer. Aromatic tertiary amines are useful as hole injection materials also. Illustrative of useful aromatic tertiary amines are the following:

1,1-bis(4-di-p-tolylaminophenyl)cyclohexane;
1,1-bis(4-di-p-tolylaminophenyl)-4-phenylcyclohexane;
1,5-bis[N-(1-naphthyl)-N-phenylamino]naphthalene;
2,6-bis(di-p-tolylamino)naphthalene;
2,6-bis[di-(1-naphthyl)amino]naphthalene;
2,6-bis[N-(1-naphthyl)-N-(2-naphthyl)amino]naphthalene;
2,6-bis[N,N-di(2-naphthyl)amine]fluorene;
4-(di-p-tolylamino)-4'-[4(di-p-tolylamino)-styryl]stilbene;
4,4'-bis(diphenylamino)quadriphenyl;
4,4"-bis[N-(1-anthryl)-N-phenylamino]-p-terphenyl;
4,4'-bis[N-(1-coronenyl)-N-phenylamino]biphenyl;
4,4'-bis[N-(1-naphthyl)-N-phenylamino]biphenyl (NPB);
4,4'-bis[N-(1-naphthyl)-N-(2-naphthyl)amino]biphenyl (TNB);
4,4"-bis[N-(1-naphthyl)-N-phenylamino]p-terphenyl;
4,4'-bis[N-(2-naphthacenyl)-N-phenylamino]biphenyl;
4,4'-bis[N-(2-naphthyl)-N-phenylamino]biphenyl;

4,4'-bis[N-(2-perylenyl)-N-phenylamino]biphenyl;
4,4'-bis[N-(2-phenanthryl)-N-phenylamino]biphenyl;
4,4'-bis[N-(2-pyrenyl)-N-phenylamino]biphenyl;
4,4'-bis[N-(3-acenaphthenyl)-N-phenylamino]biphenyl;
4,4'-bis[N-(3-methylphenyl)-N-phenylamino]biphenyl (TPD);
4,4'-bis[N-(8-fluoranthenyl)-N-phenylamino]biphenyl;
4,4'-bis[N-(9-anthryl)-N-phenylamino]biphenyl;
4,4'-bis{N-phenyl-N-[4-(1-naphthyl)-phenyl]amino}biphenyl;
4,4'-bis[N-phenyl-N-(2-pyrenyl)amino]biphenyl;
4,4',4''-tris[(3-methylphenyl)phenylamino]triphenylamine (m-TDATA);
Bis(4-dimethylamino-2-methylphenyl)-phenylmethane;
N-phenylcarbazole;
N,N'-bis[4-([1,1'-biphenyl]-4-ylphenylamino)phenyl]-N,N'-di-1-naphthalenyl-[1,1'-biphenyl]-4,4'-diamine;
N,N'-bis[4-(di-1-naphthalenylamino)phenyl]-N,N'-di-1-naphthalenyl-[1,1'-biphenyl]-4,4'-diamine;
N,N'-bis[4-[(3-methylphenyl)phenylamino]phenyl]-N,N'-diphenyl-[1,1'-biphenyl]-4,4'-diamine;
N,N-bis[4-(diphenylamino)phenyl]-N',N'-diphenyl-[1,1'-biphenyl]-4,4'-diamine;
N,N'-di-1-naphthalenyl-N,N'-bis[4-(1-naphthalenylphenylamino)phenyl]-[1,1'-biphenyl]-4,4'-diamine;
N,N'-di-1-naphthalenyl-N,N'-bis[4-(2-naphthalenylphenylamino)phenyl]-[1,1'-biphenyl]-4,4'-diamine;
N,N,N-tri(p-tolyl)amine;
N,N,N',N'-tetra-p-tolyl-4-4'-diaminobiphenyl;
N,N,N',N'-tetraphenyl-4,4'-diaminobiphenyl;
N,N,N',N'-tetra-1-naphthyl-4,4'-diaminobiphenyl;
N,N,N',N'-tetra-2-naphthyl-4,4'-diaminobiphenyl; and
N,N,N',N'-tetra(2-naphthyl)-4,4''-diamino-p-terphenyl.

Another class of useful hole-transporting materials includes polycyclic aromatic compounds as described in EP 1 009 041. Tertiary aromatic amines with more than two amine groups can be used including oligomeric materials. In addition, polymeric hole-transporting materials are used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

The thickness of HTL 140 is in the range of from 5 nm to 200 nm, preferably, in the range of from 10 nm to 150 nm.

Typically the LEL 150 includes at least one host (or host material) doped with at least one dopant (or dopant material). The host in the LEL is an electron-transporting, hole-transporting, or another material or combination of materials that support hole-electron recombination. The dopant is typically chosen from highly fluorescent green dyes. Dopants are typically incorporated at 0.01 to 20% level by volume of the host material. Preferably, dopants are incorporated into the LEL at a concentration of 0.1 to 10% by volume.

Metal complexes of 8-hydroxyquinoline (oxine) and similar derivatives constitute one class of useful host materials capable of supporting electroluminescence. Illustrative of useful chelated oxinoid compounds are the following:

CO-1: Aluminum trisoxine [alias, tris(8-quinolinolato)aluminum(III)]
CO-2: Magnesium bisoxine [alias, bis(8-quinolinolato)magnesium(II)]
CO-3: Bis[benzo{f}-8-quinolinolato]zinc (II)
CO-4: Bis(2-methyl-8-quinolinolato)aluminum(III)-μ-oxo-bis(2-methyl-8-quinolinolato) aluminum(III)
CO-5: Indium trisoxine [alias, tris(8-quinolinolato)indium]
CO-6: Aluminum tris(5-methyloxine) [alias, tris(5-methyl-8-quinolinolato) aluminum(III)]
CO-7: Lithium oxine [alias, (8-quinolinolato)lithium(I)]
CO-8: Gallium oxine [alias, tris(8-quinolinolato)gallium (III)]
CO-9: Zirconium oxine [alias, tetra(8-quinolinolato)zirconium(IV)].

Other classes of useful host materials in the LEL 150 include, but are not limited to, anthracene derivatives, such as those described in U.S. Pat. Nos. 5,935,721; 5,972,247; 6,465,115; 6,534,199; 6,713,192, U.S. Patent Application Publication Nos. 2002/0048687 A1; 200/30072966 A1, and WO 2004018587. Common examples include 9,10-bis(2-naphthalenyl)anthracene (AD-N), 2-(1,1-dimethyethyl)-9,10-bis(2-naphthalenyl)anthracene (TBADN). Other examples include different derivatives of AD-N, such as those represented by Formula E

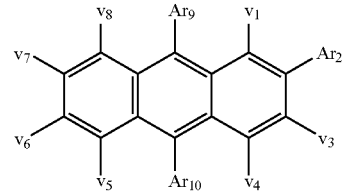

wherein:
Ar$_2$, Ar$_9$, and Ar$_{10}$ independently represent an aryl group;
v$_1$, v$_3$, v$_4$, v$_5$, v$_6$, v$_7$, and v$_8$ independently represent hydrogen or a substituent;
and Formula F

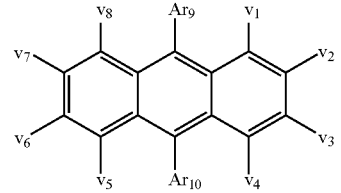

wherein:
Ar$_9$, and Ar$_{10}$ independently represent an aryl group;
v$_1$, v$_2$, v$_3$, v$_4$, v$_5$, v$_6$, v$_7$, and v$_8$ independently represent hydrogen or a substituent.

More specific examples of this class of host materials are represented by:

E-1

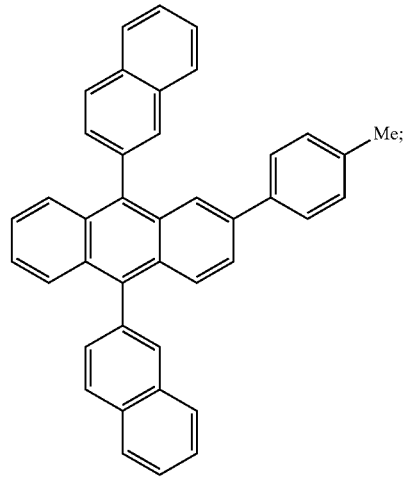

E-2
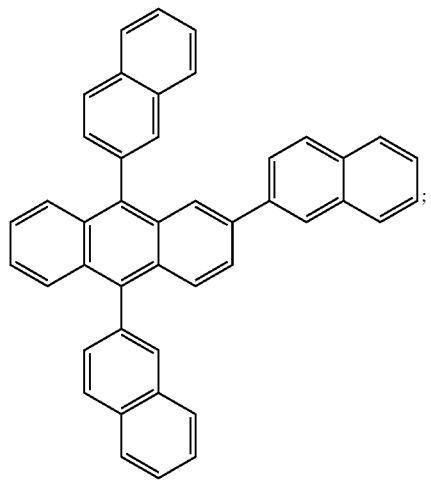
E-3
E-4
E-5
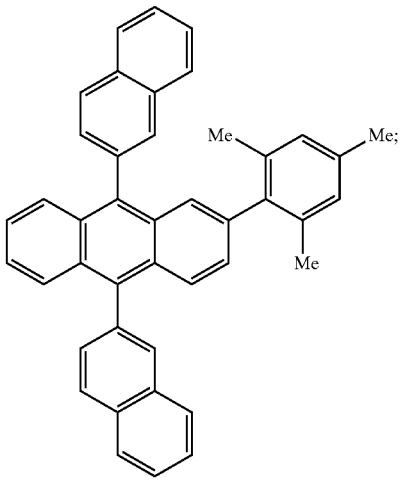
E-6
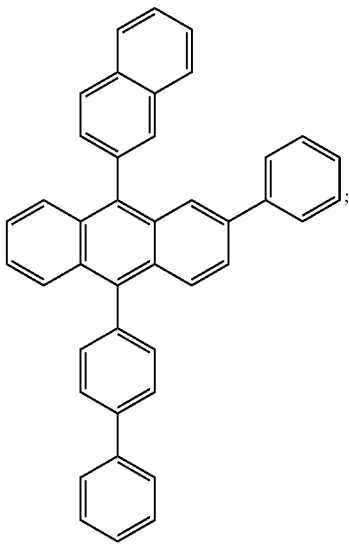
E-7
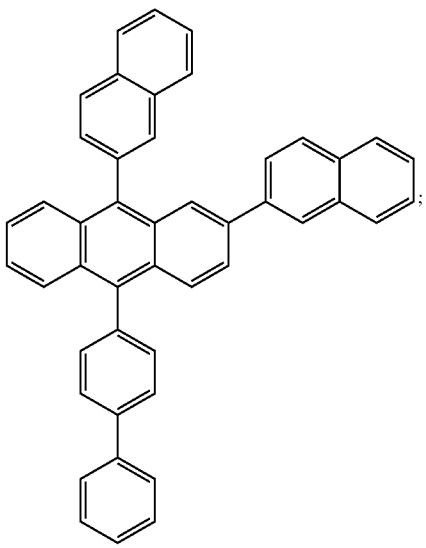

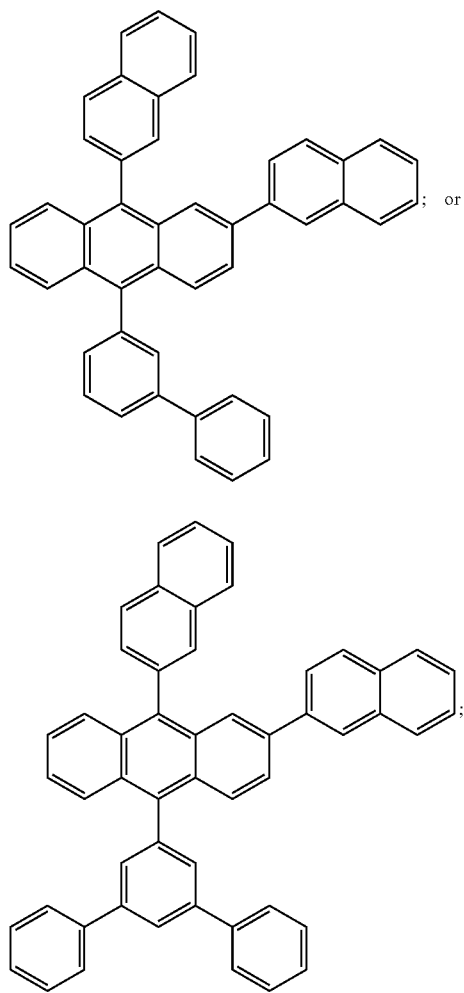
E-8
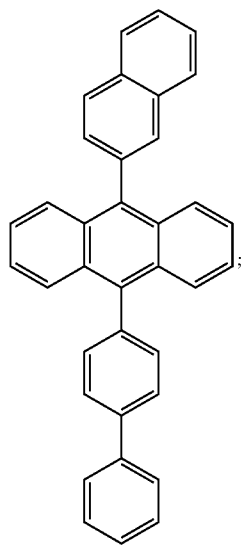
and represented by:
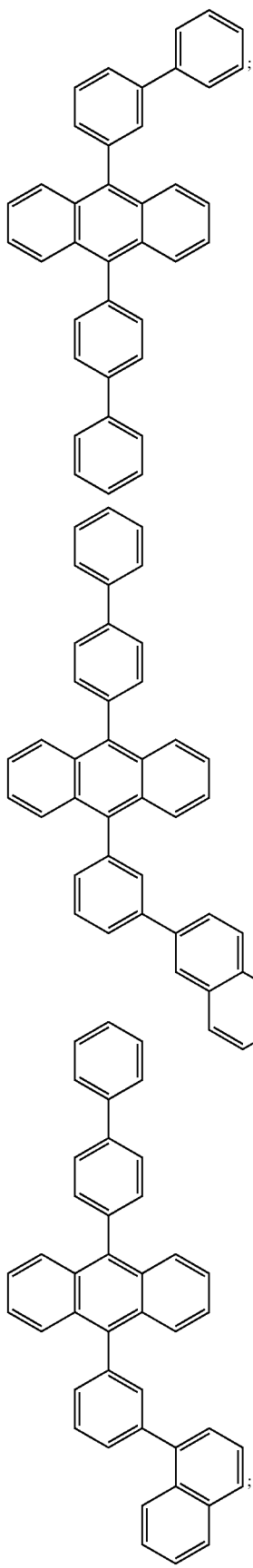
F-1
F-2
F-3
F-4

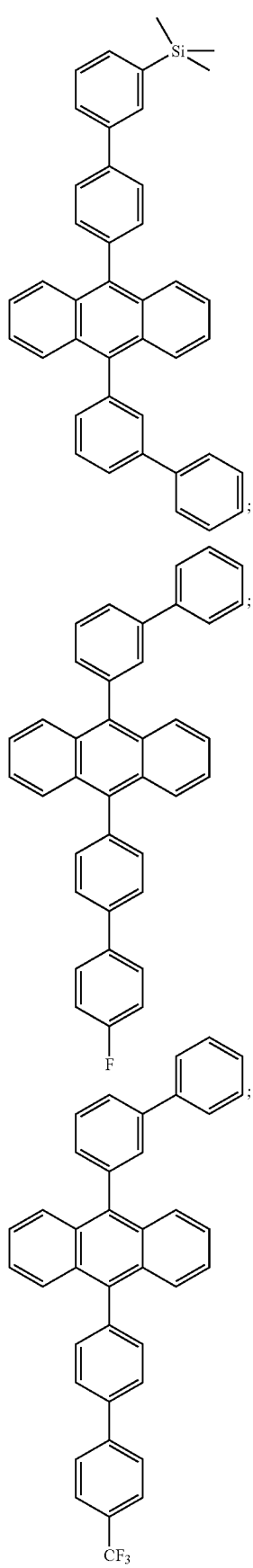
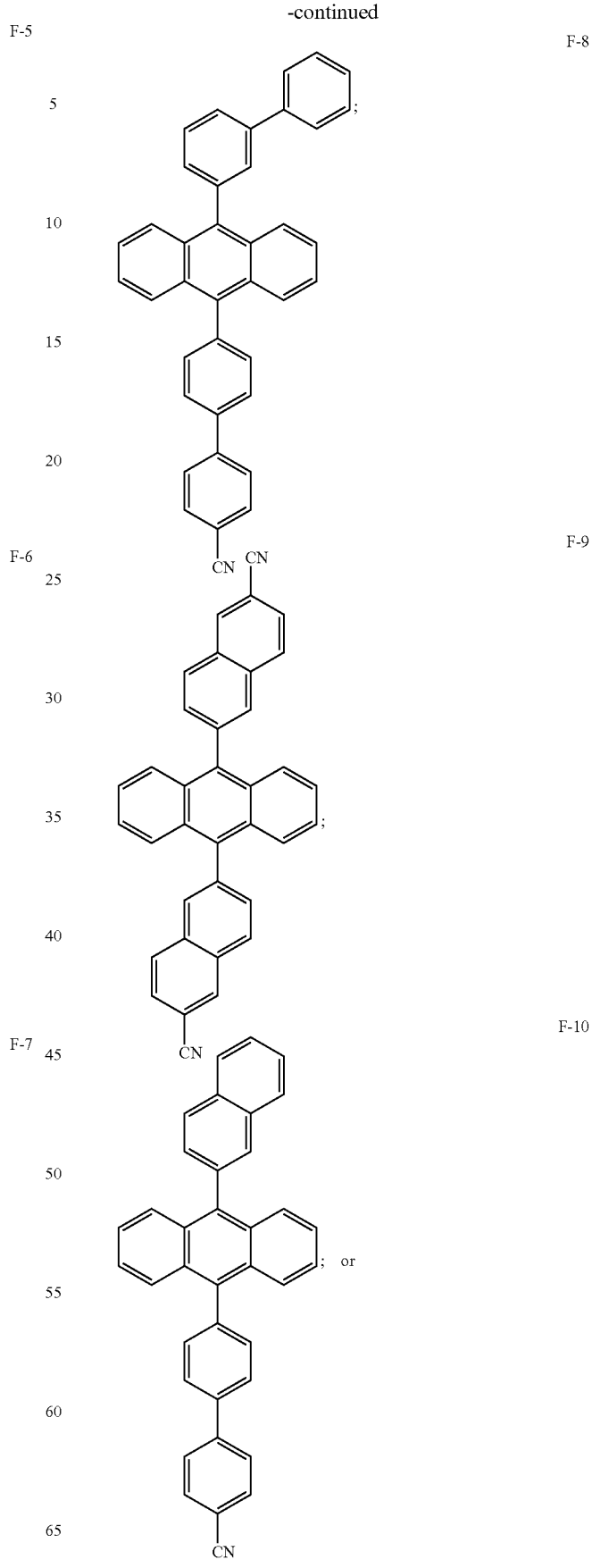

-continued

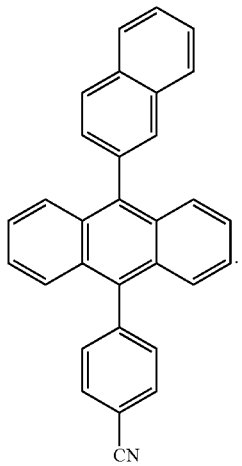

F-11

Desirable host materials are capable of forming a continuous film. The LEL can contain more than one host material in order to improve the device's film morphology, electrical properties, light emission efficiency, and operational lifetime. Mixtures of electron-transporting and hole-transporting materials are known as useful hosts. In addition, mixtures of the above listed host materials with hole-transporting or electron-transporting materials can make suitable hosts.

For efficient energy transfer from the host to the dopant material, a necessary condition is that the bandgap of the dopant is smaller than that of the host material. Preferably, the bandgap of the host encloses that of the dopant, or the HOMO and the LUMO of the dopant are positioned within the bandgap of the host. Ideally, the energy difference between the HOMO of the host and the HOMO of the dopant should be less than 0.5 eV, and the energy difference between the LUMO of the host and the LUMO of the dopant should be less than 0.5 eV.

Useful fluorescent green dopants include, but are not limited to, derivatives of coumarin, rhodamine, quinacridone, and anthracene. Illustrative examples of useful materials include, but are not limited to, the following:

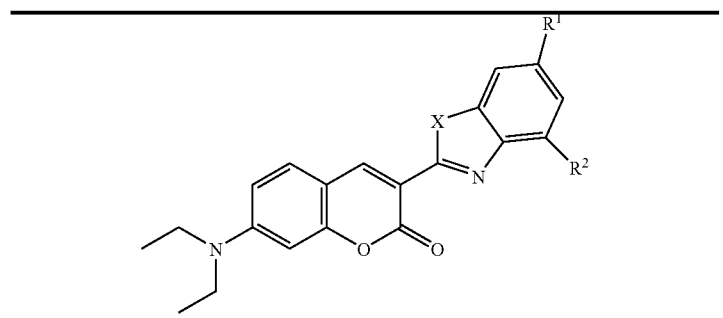

|     | X | R1     | R2      |
|-----|---|--------|---------|
| L1  | O | H      | H       |
| L2  | O | H      | Methyl  |
| L3  | O | Methyl | H       |
| L4  | O | Methyl | Methyl  |
| L5  | O | H      | t-butyl |
| L6  | O | t-butyl| H       |
| L7  | O | t-butyl| t-butyl |
| L8  | S | H      | H       |
| L9  | S | H      | Methyl  |
| L10 | S | Methyl | H       |
| L11 | S | Methyl | Methyl  |
| L12 | S | H      | t-butyl |
| L13 | S | t-butyl| H       |
| L14 | S | t-butyl| t-butyl; |

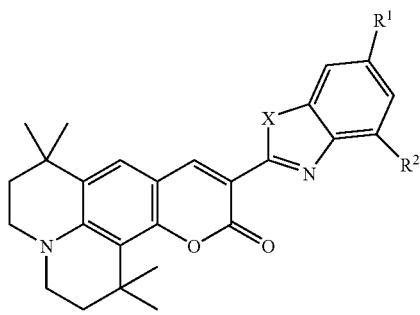

|     | X | R1     | R2     |
|-----|---|--------|--------|
| L15 | O | H      | H      |
| L16 | O | H      | Methyl |
| L17 | O | Methyl | H      |
| L18 | O | Methyl | Methyl |

-continued
| | | | |
|---|---|---|---|
| L19 | O | H | t-butyl |
| L20 | O | t-butyl | H |
| L21 | O | t-butyl | t-butyl |
| L22 | S | H | H |
| L23 | S | H | Methyl |
| L24 | S | Methyl | H |
| L25 | S | Methyl | Methyl |
| L26 | S | H | t-butyl |
| L27 | S | t-butyl | H |
| L28 | S | t-butyl | t-butyl; |
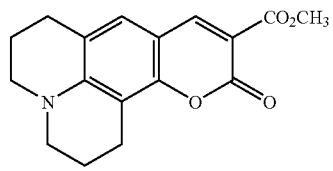
L29
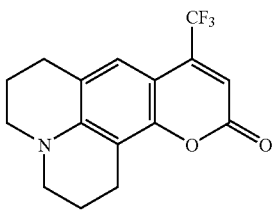
L30
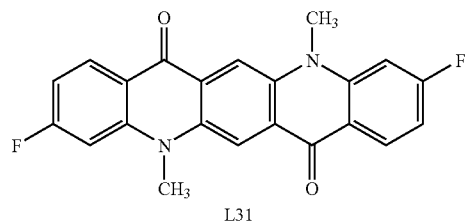
L31
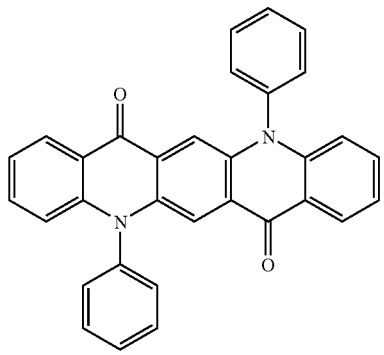
L32
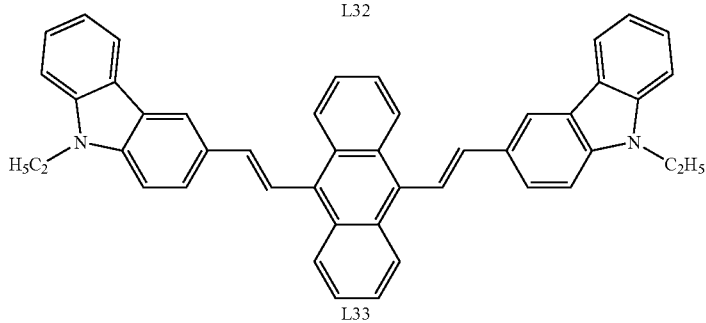
L33
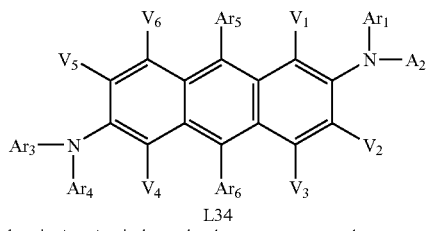
L34
wherein $Ar_1$-$Ar_6$ independently represent an aryl group; and $v_1$-$v_7$ independently represent hydrogen or a substituent.

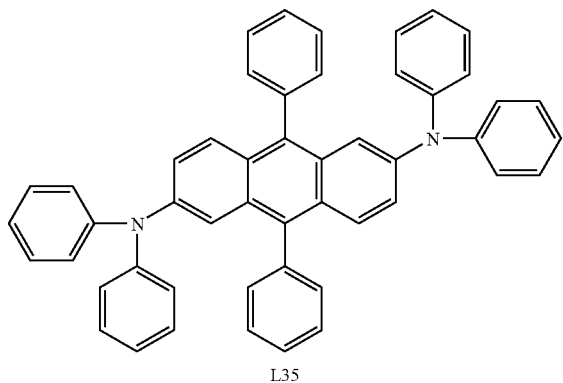
L35
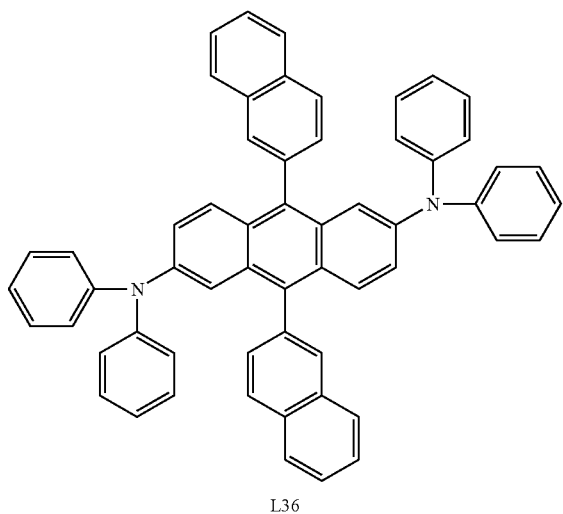
L36
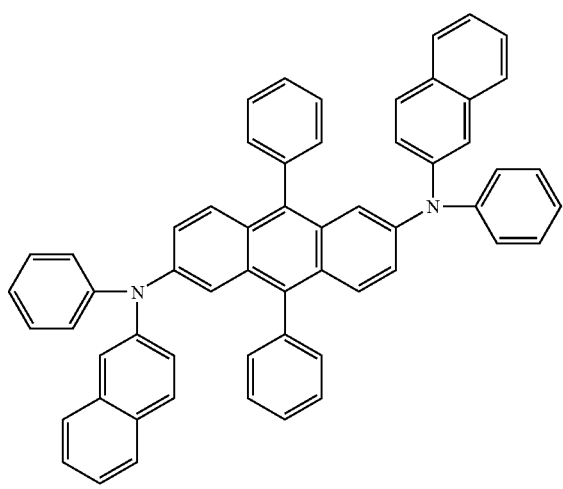
L37

The thickness of each LEL is in the range of from 5 nm to 100 nm, preferably, in the range of from 5 nm to 50 nm.

The invention forms the ETL 160 using azatriphenylene derivative represented by Formula I:

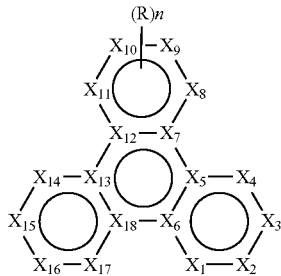

wherein X1 to X18 are individually the same or different and where X5-X7, X12-X13 and X18 are all carbon and, where one of X1-X4 is a nitrogen, one of X8-X11 is a nitrogen and one of X14-X17 is a nitrogen; R is a hydrogen or a substituent and is independently selected from hydrogen, an alkyl group, a cycloalkyl group, a heterocyclic group, an alkenyl group, a cycloalkenyl group, an alkynyl group, a hydroxyl group, a mercapto group, an alkoxy group, an alkylthio, an aryl group, a heteroaryl group, an amino group, a cyano group, a nitro group, an alkylthio group, an aralkyl group, an aryloxy group, an arylthio group, a halogen, a silyl group, a siloxanyl group, an formyl group, an acyloxy group, a carboxyl group, an imino group, an acyl group, a carbamoyl group, a carbonamido group, a sulfamoyl group, a sulfonyl group, a sulfinyl group, a sulfonyloxy group, a phosphate group, a phosphate group, and a cyclic structure formed with an adjacent substitutent group; R represent more than one substituents provided at any available positions in the azatriphenylene skeletal structure. In the case of where there is a plurality of substitutents, the substituents may be the same or different; n is integer of from 1 to 11 and when n is 2 or more the R substituents can form a fused ring structure; and when R contains carbon atoms it can have from 1 to 48 carbon atoms.

Preferably, X1 is a nitrogen atom, or X1 and X17 are nitrogen atoms, or X1 and X14 are nitrogen atoms, or X1 and X4 are nitrogen atoms, or X1, X4, and X8 are nitrogen atoms, or X1, X11 and X17 are nitrogen atoms. The most preferable is where X1 and X17 and either X8 or X11 are nitrogen.

In order to prevent the material from crystallization, preferably, the aforementioned azatriphenylene derivative has unsymmetrical structure. For example, if R represent more than one substituent, the number of the same substituents should be odd. If the number of the same substituents is even, the position of the nitrogen atoms from X1 to X18 should be arranged unsymmetrically.

The electron energy structure of the azatriphenylene derivatives can be affected by the number of the nitrogen atoms in the position from X1 to X18. The LUMO level will decrease by increasing the number of the nitrogen atoms within the position of from X1 to X18. For the application to form OLEDs, in order not to form a high barrier for electron injection from the ETL into the LEL, the total number of the nitrogen atoms within the position of from X1 to X18 should be 3.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, 2-bromoethyl, 3-chlorobutyl, trifluoromethyl, ethyl, t-butyl, 3-(2,4-di-t-pentylphenoxy) propyl, and tetradecyl, cyclohexyl, cyclopentyl; alkenyl and cylcloalkenyl, such as ethylenyl, 2-butenyl, cyclohexenyl, and cyclopentenyl; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; alkynyl, such as ethylnyl, propylnyl, 3-bromobutylnyl, and butylnyl; aryl such as styryl, phenyl, 4-t-butylphenyl, 2,4,6-trimethylphenyl, xylenyl, tolyl, naphthyl, biphenyl, anthryl, fluorenyl, benzofluorenyl, dibenzofluorenyl, phenanthrenyl, spirofluorenyl, perylenyl, and pyrenyl; aralkyl, such as benzyl, phenylpropyl, and naphthylethyl; aryloxy, such as phenoxy, 2-methylphenoxy, alpha- or beta-naphthyloxy, and 4-tolyloxy; arylthio, such as phenylthio, naphthylthio, and tolylthio; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxopyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as methylthio, ethylthio, propylthio, cyclohexylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amino, such as phenylanilino, 2-chloroanilino, diethylamino, dodecylamino; imino, such as 1 (N-phenylimido)ethyl, N-succinimido, and 3-benzylhydantoinyl; phosphate, such as dimethylphosphate and ethylbutylphosphate; phosphite, such as diethyl and dihexylphosphite; a heteraryl group, heterocyclic group, a heterocyclic oxy group or a heterocyclic thio group, each of which may be substituted and which contain a 3- to 7-membered heterocyclic ring composed of carbon atoms and at least one hetero atom selected from the group consisting of oxygen, nitrogen, sulfur, phosphorous, or boron, such as furyl, thienyl, 2-benzimidazolyloxy or 2-benzothiazolyl, pyridyl, pyrrolyl, bithienyl, benzofuryl, benzimidazolyl, benzoxazolyl, quinoxalinyl, quinolyl, diphenyloxadiazolyl, diphenylthiodiazolyl, phenanthrolyl, pytrolyl, phenazinyl, pyridazinyl, caryldinyl and carbazolyl; quaternary ammonium, such as triethylammonium; quaternary phosphonium, such as triphenylphosphonium; silyloxy, such as trimethylsilyloxy; and silyl, such as trimethylsilyl, triethylsilyl, t-butyldimethylsily, and triethoxylsilyl.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

Preferably, R is an aryl group such as styryl, phenyl, 4-t-butylphenyl, 2,4,6-trimethylphenyl, xylenyl, tolyl, naphthyl, biphenyl, anthryl, fluorenyl, benzofluorenyl, dibenzofluorenyl, phenanthrenyl, spirofluorenyl, perylenyl, and pyrenyl, or a heteroaryl group such as furyl, thienyl, 2-benzimidazolyloxy or 2-benzothiazolyl, pyridyl, pyrrolyl, bithienyl, benzofuryl, benzimidazolyl, benzoxazolyl, quinoxalinyl, quinolyl, diphenyloxadiazolyl, diphenylthiodiazolyl, phenanthrolyl, pytrolyl, phenazinyl, pyridazinyl, caryldinyl and carbazolyl; or an alkyl group such as trifluoromethyl, methyl, ethyl, propyl, isopropyl, butyl, isobutyl, t-butyl, pentyl, hexyl, ethylhexyl, heptyl, octyl, nonyl, decyl, dodecyl, hexadecyl, cyclohexyl, cyclopentyl, 3,7-dimethyloctyl; or an alkoxy group such as 3,7-dimethyloctyloxy, methoxy, ethoxy, butoxy, methoxyethoxyethyl, methoxyethyloxyethoxyethyl, hexyloxy, and ethylhexyloxy; or an amino group such as diphenylamino, ditolylamino, di-(4-t-butylphenyl)amino, dimethoxyphenylamino, and di-(methoxycarbonylphenyl) amino; or a halogen such as chloro, bromo, and fluoro; or a cyano group, or a nitro group. More preferably, R is an aryl group such as phenyl, 4-t-butylphenyl, tolyl, naphthyl, biphenyl, anthryl, fluorenyl, benzofluorenyl, phenanthrenyl, spirofluorenyl, and perylenyl; or a heteroaryl group such as furyl, thienyl, pyridyl, pyrrolyl, bithienyl, benzimidazolyl, benzoxazolyl, quinoxalinyl, quinolyl, diphenyloxadiazolyl, phenanthrolyl, and carbazolyl; or an alkyl group such as trifluoromethyl, methyl, hexyl, ethylhexyl, heptyl, octyl, 3,7-dimethyloctyl; or an alkoxy group such as 3,7-dimethyloctyloxy, methoxy, hexyloxy, and ethylhexyloxy; or an amino group such as diphenylamino, ditolylamino, di-(4-t-butylphenyl)amino, or a halogen such as fluoro; or a cyano group.

In one aspect of the present invention, the azatriphenylenes are molecular compounds; that is they are not polymeric. The azatriphenylenes of the invention are small molecules with molecular weights typically below 1500, preferably below 1000.

In another aspect of the present invention provides a polymer having an azatriphenylene structure represented by Formula I as part of a repeating unit. The polymer is useful in electron-transporting layer in an OLED:

The organic compound of the present invention may contain a plurality of parent azatriphenylene skeletal structure represented by Formula I, and the plurality of parent azatriphenylene skeletal structure is connected together by a connecting unit W represented by Formula II.

$$W-[\text{Formula I}]_m \qquad \text{Formula II}$$

Wherein W is a connecting unit including alkyl, aryl, and heteroaryl group that conjugately or unconjugately connects the multiple azatriphenylene groups together; and m is an integer of from 2 to 8.

W includes the following groups:

Group 1:

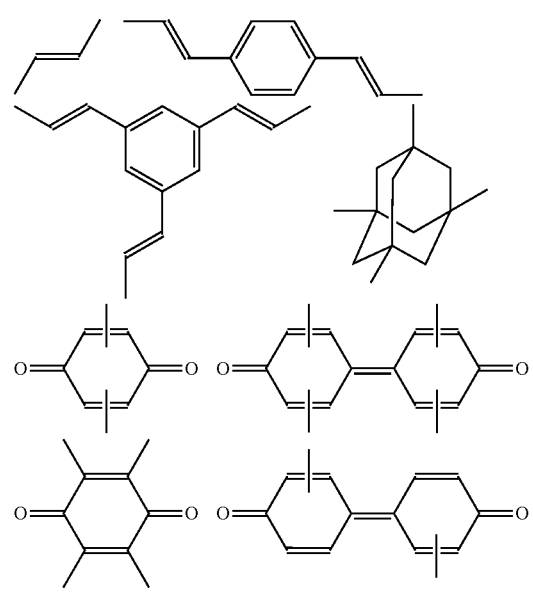

Group 2:

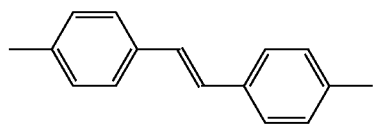

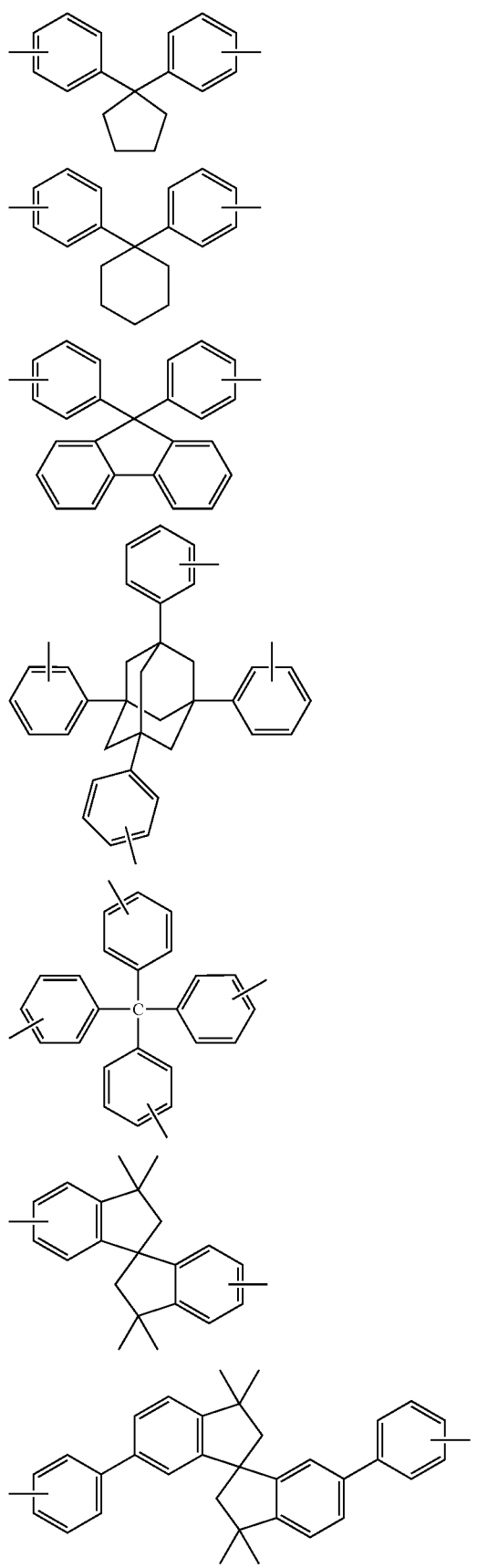
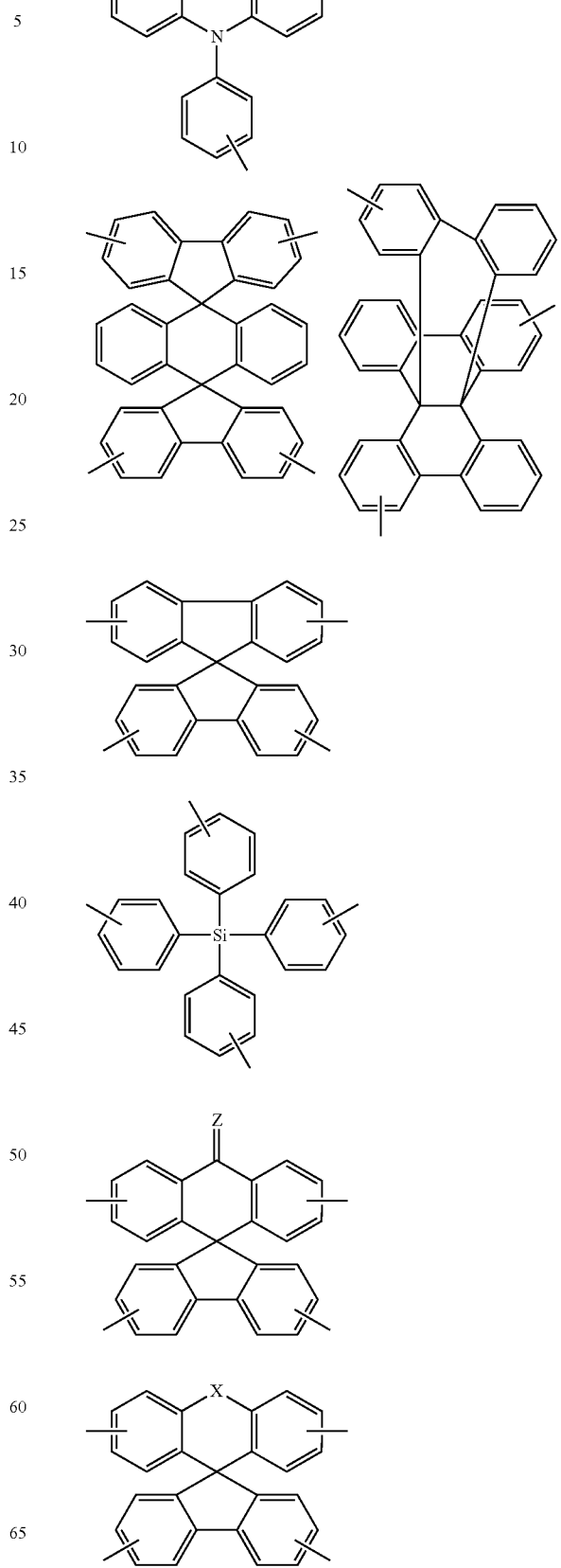

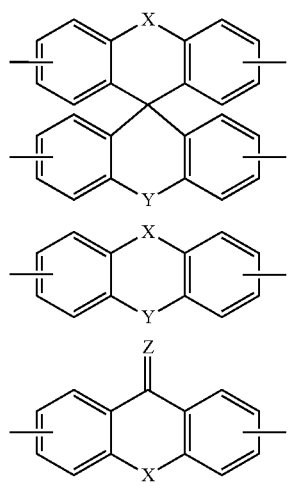
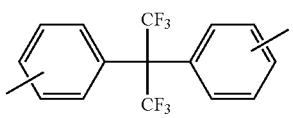
wherein: Z is O or C(CN)$_2$, X and Y are each individually O, S, SO$_2$, CH$_2$, CHR$^1$, CR$^1$R$^2$, or NR$^1$, and R$^1$ and R$^2$ are individually hydrogen, or alkyl group of from 1 to 24 carbon atoms, or aryl group of from 6 to 24 carbon atoms, or heteroaryl group of from 4 to 24 carbon atoms, or halogen atom, or atoms necessary to complete a fused aromatic ring.
Group 3:
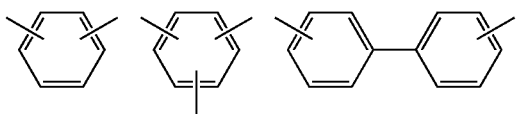
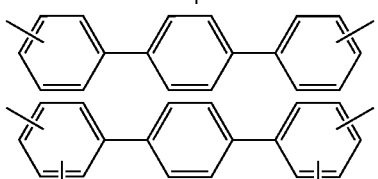
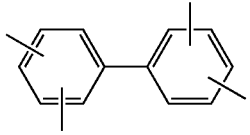
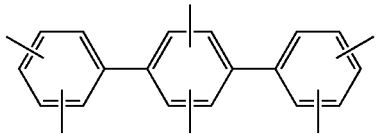
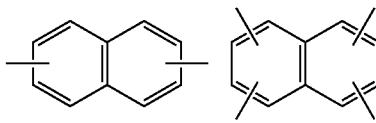
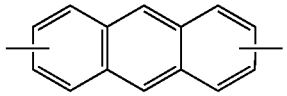
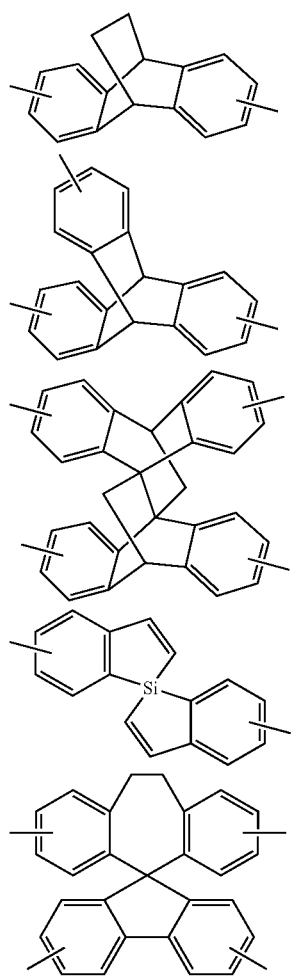
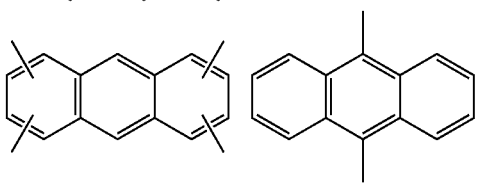
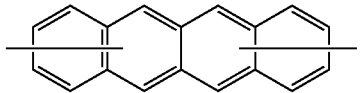
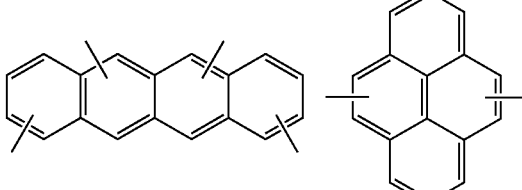
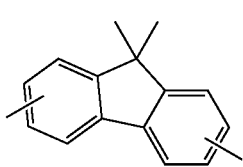

-continued
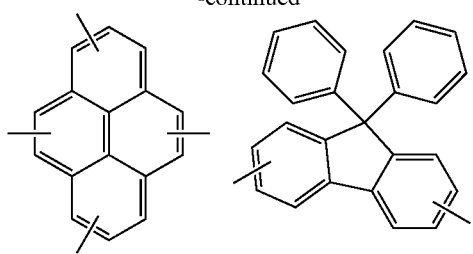
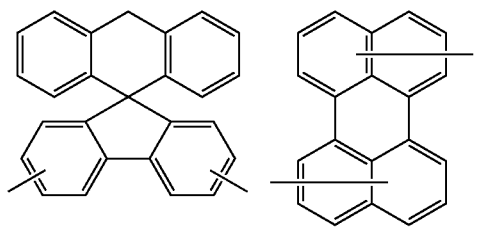
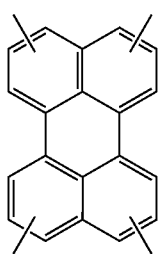
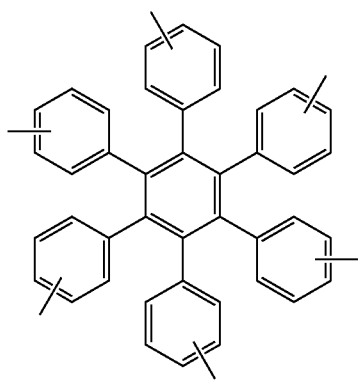
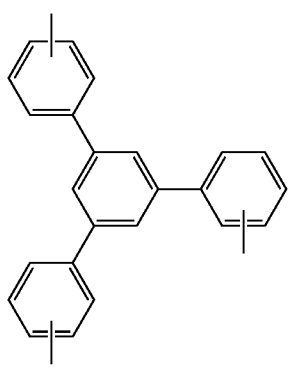
-continued
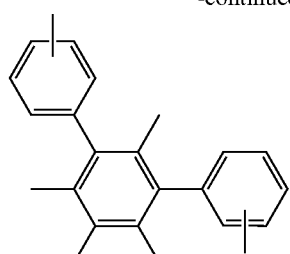
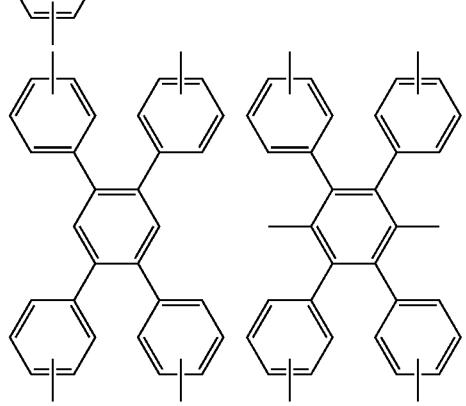
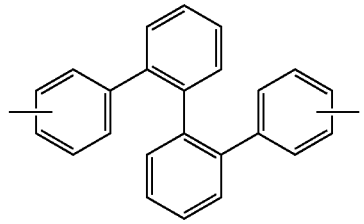
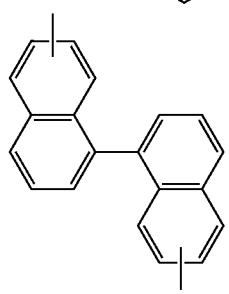
Group 4:
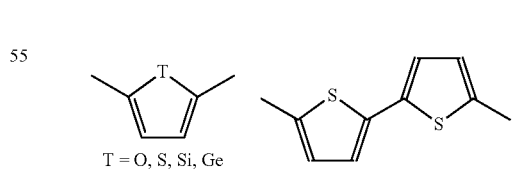
T = O, S, Si, Ge
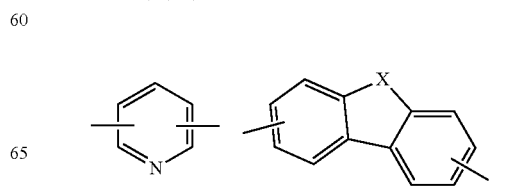

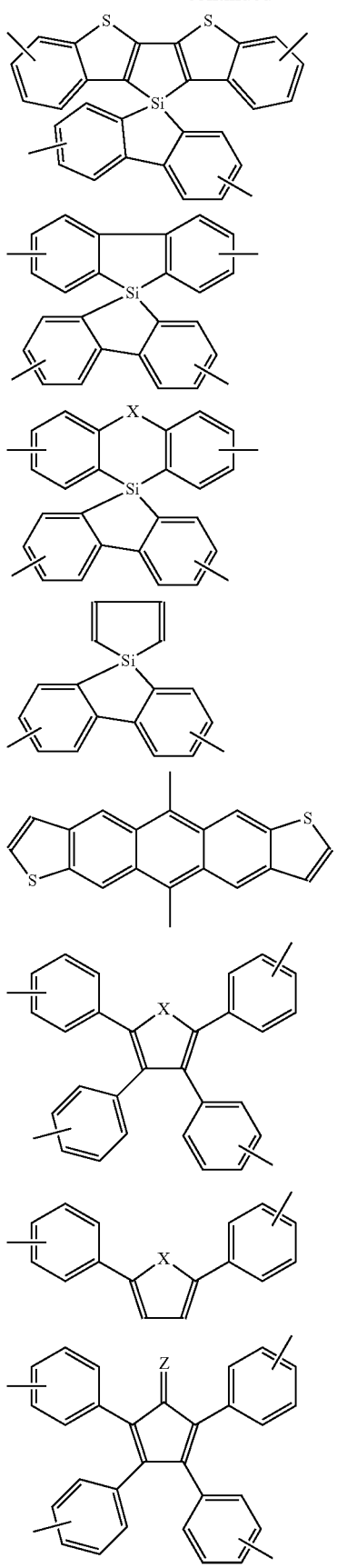
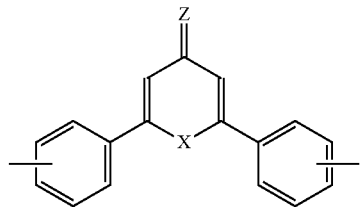
The following chemical structures constitute specific examples of preferred azatriphenylenes satisfying the requirement of the invention:
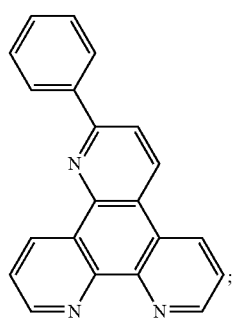
I-1
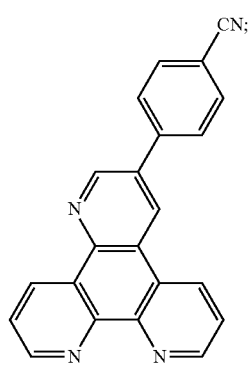
I-2
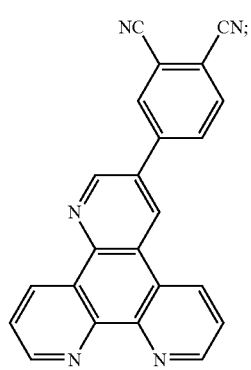
I-3

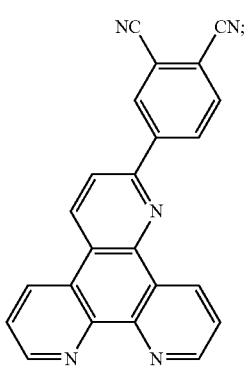

I-4

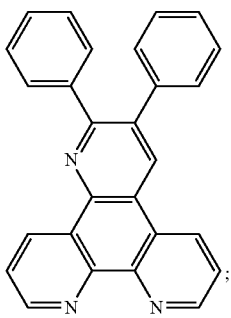

I-5

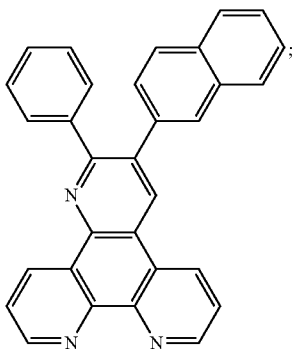

I-6

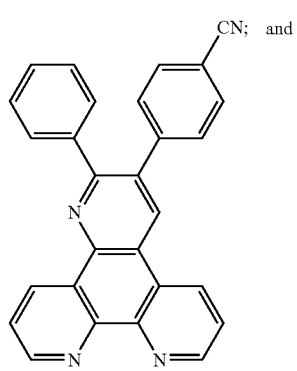

I-7

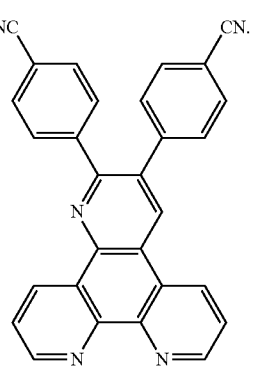

I-8

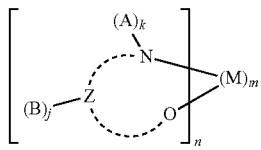

I-9

An n-type doped organic layer is also useful for the ETL as described in U.S. Pat. No. 6,013,384. An n-type doped organic layer means that the layer is electrically conductive, and the charge carriers are primarily electrons. The conductivity is provided by the formation of a charge-transfer complex as a result of electron transfer from the dopant material to the host material. In this case, the ETL contains azatriphenylene derivatives and the n-type dopant material. The n-type dopant material, for example, is Li, Na, K, Rb, Cs, Mg, Ca, Sr, Ba, La, Ce, Nd, Sm, Eu, Tb, Dy, or Yb.

The thickness of each ETL is in the range of from 5 nm to 200 nm, preferably, in the range of from 5 nm to 100 nm.

In some cases, there is a need to form an EIL 170 over the ETL 160. EIL 170 can include alkaline metal complexes or alkaline earth metal complexes. Wherein, the metal complex in the electron-injecting layer includes a cyclometallated complex represented by Formula G $$\left[ \begin{array}{c} (A)_k \\ \vdots \\ (B)_j - Z \end{array} \right]_n (M)_m$$

wherein:

Z and the dashed arc represent two or three atoms and the bonds necessary to complete a 5- or 6-membered ring with M;

each A represents H or a substituent and each B represents an independently selected substituent on the Z atoms, provided that two or more substituents may combine to form a fused ring or a fused ring system;

j is 0-3 and k is 1 or 2;

M represents an alkali metal or an alkaline earth metal; and m and n are independently selected integers selected to provide a neutral charge on the complex.

Illustrative examples of useful electron-injecting materials include, but are not limited to, the following:

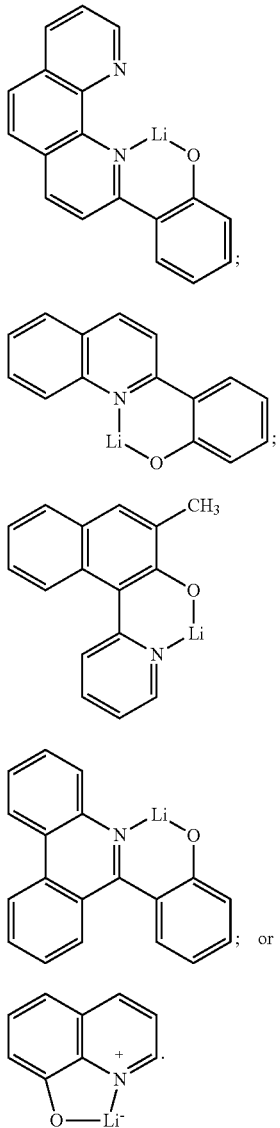

The EIL 170 can also be doped or mixed with other materials. The EIL 170 has the thickness in the range of from 0.5 nm to 10 nm.

The organic materials in the OLEDs mentioned above are suitably deposited through a vapor-phase method such as thermal evaporation, but are deposited from a fluid, for example, from a solvent with an optional binder to improve film formation. The material to be deposited by thermal evaporation is vaporized from an evaporation "boat" often including a tantalum material, e.g., as described in U.S. Pat. No. 6,237,529, or is first coated onto a donor sheet and then sublimed in closer proximity to the substrate. Layers with a mixture of materials can use separate evaporation boats or the materials are premixed and coated from a single boat or donor sheet. For full color display, the pixelation of LELs can be needed. This pixelated deposition of LELs is achieved using shadow masks, integral shadow masks, U.S. Pat. No. 5,294,870, spatially defined thermal dye transfer from a donor sheet, U.S. Pat. Nos. 5,688,551; 5,851,709, and 6,066,357, and inkjet method, U.S. Pat. No. 6,066,357.

When light emission is viewed solely through the anode, the cathode 180 can be transparent, opaque, or reflective. Desirable materials have effective film-forming properties to ensure effective contact with the underlying organic layer, promote electron injection at low voltage, and have effective stability. Useful cathode contain a metal capable of reducing the metal ions in EIL 170, such as, Al, Zr, Ti, Y, and Sc. One preferred cathode is Al cathode. Useful cathode can also contain a low work function metal with a work function less than 4.0 eV or metal alloy. One preferred cathode material includes a Mg:Ag alloy as described in U.S. Pat. No. 4,885,221. When the cathode includes a low work function metal layer with a work function less than 4.0 eV, wherein the thickness of the low work function metal layer is in a range of from 0.5 nm to 20 nm, a metal capping layer is disposed on top of the low work function metal layer for the protection of the underneath low work function metal layer. When light emission is viewed through the cathode, cathode 180 should be transparent or nearly transparent. For such applications, metals should be thin or one should use transparent conductive oxides, or include these materials. Optically transparent cathodes have been described in more detail in U.S. Pat. Nos. 4,885,211; 5,247,190; 5,703,436; S 5,608,287; 5,837,391; 5,677,572; 5,776,622; 5,776,623; 5,714,838; 5,969,474; 5,739,545; 5,981,306; 6,137,223; 6,140,763; 6,172,459; 6,278,236; 6,284,393, and EP 1 076 368. Cathode materials are typically deposited by thermal evaporation, electron beam evaporation, ion sputtering, or chemical vapor deposition. When needed, patterning is achieved through many well known methods including, but not limited to, through-mask deposition, integral shadow masking, for example as described in U.S. Pat. No. 5,276,380 and EP 0 732 868, laser ablation, and selective chemical vapor deposition.

Most OLEDs are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiOx, Teflon, and alternating inorganic/polymeric layers are known in the art for encapsulation.

Polymer materials can be formed by using Formula I as a part of a repeating unit. The polymers of the present invention can be used in emissive layer, and doped with one or more fluorescent dyes, phosphorescent dopants, or other light emitting materials, or used without dopants, or the polymers can be used as charge transport materials, or can be used both as charge transport materials and emissive materials.

The aforementioned OLEDs prepared in accordance with the present invention are useful for display applications. OLED displays or other electronic devices can include a plurality of OLEDs as described above.

In addition, the aforementioned azatriphenylene derivatives represented by Formula I and Formula II, can also be useful in other kind of organic electronic devices, such as organic thin film transistors and organic photovoltaic cells.

EXAMPLES

Synthesis of Molecules

A typical synthesis is illustrated in Scheme 1.

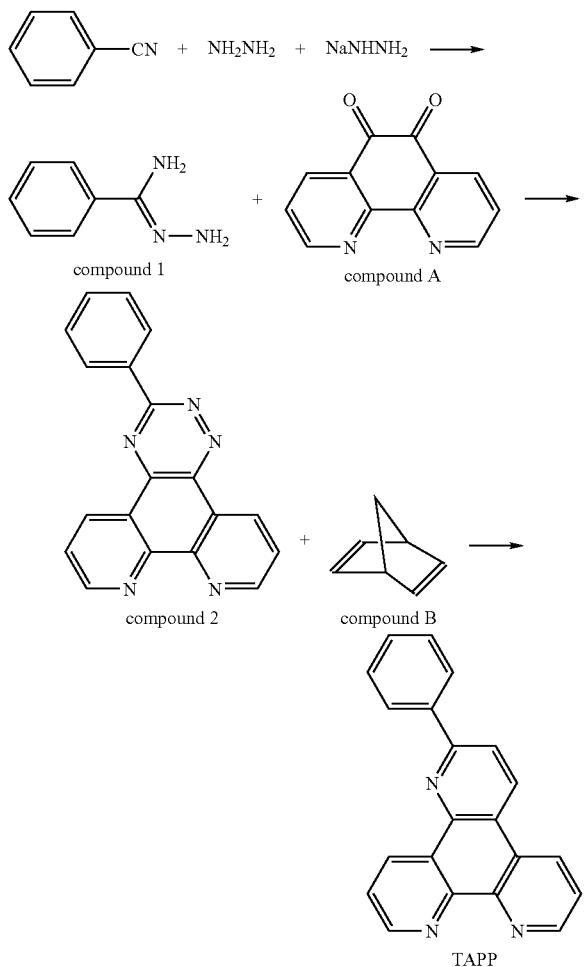

Example 1

Synthesis of Compound 1

Sodium hydrazide (37.4 g, 0.69 mol) was made in situ from sodium and hydrazine in 100 mL of dry ether and 150 mL of isopropyl ether was added. To the reaction was added dry hydrazine (22.5 g, 0.70 mol) and benzonitrile (23.6 g, 0.23 mol) in 60 mL of isopropyl ether was added dropwise. The reaction became thick and light yellow precipitate formed. The reaction was heated at 55° C. for 2 hours. The reaction was quenched with 100 mL of water slowly, and light tan precipitate formed at the interface. The aqueous layer was saturated with potassium carbonate. The precipitate was filtered, dissolved in ethyl acetate, and dried over magnesium sulfate. The solvent was removed to give 28.5 g (92% yield) product as light beige hard solid. $^1$H NMR (d$_6$-acetone) (δ in ppm): 4.32 (br, 2H), 4.75 (br, 2H), 5.45 (br, 1H), 7.34-7.41 (m, 3H), 7.60-7.63 (m, 2H), 7.78-7.81 (m, 1H).

Example 2

Synthesis of Compound 2

Compound A (5.0 g, 0.022 mol) was suspended in 250 mL of ethanol and heated to reflux to be dissolved. Compound 1 (3.0 g, 0.022 mol) was added as solid. The reaction became clear in 5 minutes, and then large amount of bright yellow precipitate formed. Reaction was heated at reflux for 3 hours and cooled down. The precipitate was filtered off and washed with cold methanol to give 7.0 g (97% yield) of pure product as bright yellow silky solid. $^1$H NMR (CDCl$_3$) (δ in ppm): 7.26-7.34 (m, 3H), 7.61-7.65 (m, 2H), 8.53-8.56 (m, 2H), 9.02-9.08 (m, 2 H), 9.41-9.46 (m, 2H).

Example 3

Synthesis of TAPP
(6-phenyl-1,5,12-triazatriphenylene, Formula I-1)

Compound 2 (7.0 g, 0.022 mol) was dissolved in 100 mL of hot o-dichlorobenze, and compound B (19.8 g, 0.22 mol) was added. The reaction was heated to reflux for 4 days. After cooling down, the reaction was poured into 600 mL of hexane and the precipitate was filtered and washed with hexane to give 6.7 g (96% yield) of crude product as light-tan fluffy solid. The crude product was sublimed to give pure product as light beige crystals. $^1$H NMR (CDCl$_3$) (δ in ppm): 7.53-7.62 (m, 3H), 7.71-7.80 (m, 2H), 8.12-8.15 (m, 1H), 8.33-8.36 (m, 2 H), 8.86-8.90 (m, 2H), 9.21-9.27 (m, 2H), 9.73-9.77 (m, 1H). DSC show Tg of 78.5° C., Tm of 202.3° C., and Tc 142.2° C.

EL Device Fabrication and Performance

The following device examples are presented for a further understanding of the present invention. During the fabrication of the OLEDs, the thickness of the organic layers and the doping concentrations were controlled and measured in situ using calibrated thickness monitors (INFICON IC/5 Deposition Controller, made by Inficon Inc., Syracuse, N.Y.). The EL characteristics of all the fabricated devices were evaluated using a constant current source (KEITHLEY 2400 SourceMeter, made by Keithley Instruments, Inc., Cleveland, Ohio) and a photometer (PHOTO RESEARCH SpectraScan PR 650, made by Photo Research, Inc., Chatsworth, Calif.) at room temperature. Operational stabilities of the devices were tested at 70° C. under the alternative current of 20 mA/cm$^2$.

Example 4

Comparative

The preparation of an OLED is as follows: A ~1.1 mm thick glass substrate coated with a transparent ITO conductive layer was cleaned and dried using a commercial glass scrubber tool. The thickness of ITO is about 42 nm and the sheet resistance of the ITO is about 68Ω/square. The ITO surface was subsequently treated with oxidative plasma to condition the surface as an anode. A layer of CFx, 1 nm thick, was deposited on the clean ITO surface as the HIL by decomposing CHF$_3$ gas in an RF plasma treatment chamber. The substrate was then transferred into a vacuum deposition chamber for deposition of all other layers on top of the substrate. The following layers were deposited in the following sequence by evaporation from a heated boat under a vacuum of approximately 10$^{-6}$ Torr:

a) an HTL, 75 nm thick, including "4,4'-bis[N-(1-naphthyl)-N-phenylamino]biphenyl" (NPB);

b) a LEL, 20 nm thick, including "tris(8-hydroxyquinoline)-aluminum" (Alq) doped with 1.0 vol % 10-(2-benzothiazolyl)-1,1,7,7-tetramethyl-2,3,6,7-tetrahydro-1H,5H,11H(1)benzopyrano(6,7,8-ij)quinolizin-11-one (C545T); and c) an ETL, 40 nm thick, including Alq.

d) approximately 210 nm thick, including Mg:Ag (formed by co-evaporation of about 95 vol. % Mg and 5 vol. % Ag).

After the deposition of these layers, the device was transferred from the deposition chamber into a dry box (VAC Vacuum Atmosphere Company) for encapsulation. The OLED has an emission area of 10 mm².

Figure 3:
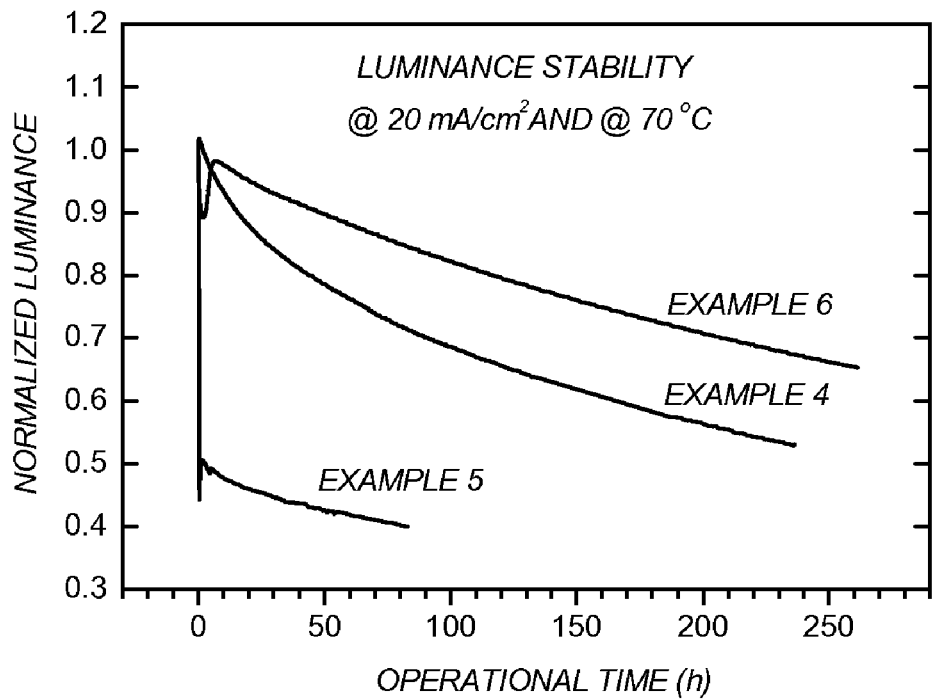
FIG. 3 is a graph, showing normalized luminance versus operational time, demonstrating the luminance stability of the OLEDs fabricated in accordance with the present invention as well as the prior art.
Figure 4:
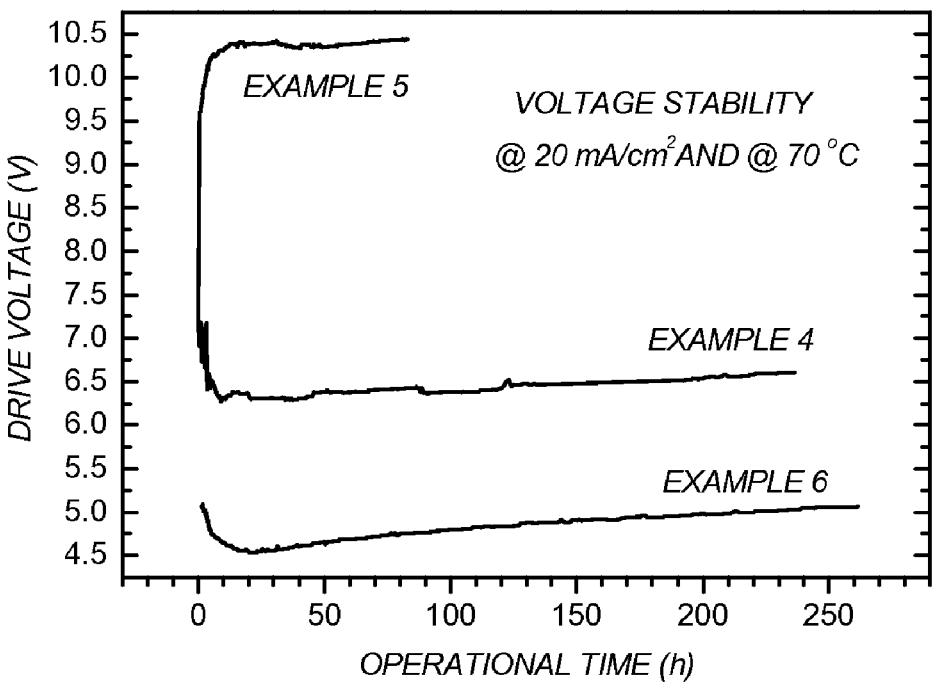
FIG. 4 is a graph, showing drive voltage versus operational time, demonstrating the voltage stability of the OLEDs fabricated in accordance with the present invention as well as the prior art.

This OLED requires a drive voltage of about 7.3 V to pass 20 mA/cm². Under this test condition, the device has a luminance of 1732 cd/m², and a luminous efficiency of about 8.7 cd/A. Its emission peak is at 524 nm and the power efficiency is about 3.8 lm/W. The EL performance is summarized in Table 1. The operational lifetime was measured as $T_{50}$(70° C.@20 mA/cm²) (i.e. a time at which the luminance retains 50% of its initial value after being operated at 70° C. and at 20 mA/cm²). Its $T_{50}$(70° C.@20 mA/cm²) is about 250 hours. The normalized luminance vs. operational time and the drive voltage vs. operational time, tested at 70° C. and at 20 mA/cm², are shown in FIGS. 3 and 4, respectively.

Example 5

Comparative

Another OLED was constructed as the same as that in Example 4, except that the ETL was replaced by a 40 nm layer of 4,7-diphenyl-1,10-phenanthroline (Bphen).

This OLED requires a drive voltage of about 7.0 V to pass 20 mA/cm². Under this test condition, the device has a luminance of 1943 cd/m², and a luminous efficiency of about 9.7 cd/A. Its emission peak is at 522 nm and the power efficiency is about 4.4 μm/W. The EL performance is summarized in Table 1. The operational lifetime was measured as $T_{50}$(70° C.@20 mA/cm²), which is less than 2 hours. The normalized luminance vs. operational time and the drive voltage vs. operational time, tested at 70° C. and at 20 mA/cm², are shown in FIGS. 3 and 4, respectively.

Example 6

Inventive

Another OLED was constructed as the same as that in Example 4, except that the ETL was replaced by a 40 nm layer of TAPP (Formula I-1).

This OLED requires a drive voltage of about 5.0 V to pass 20 mA/cm². Under this test condition, the device has a luminance of 1840 cd/m², and a luminous efficiency of about 9.2 cd/A. Its emission peak is at 522 nm and the power efficiency is about 5.8 μm/W. The EL performance is summarized in Table 1. The operational lifetime was measured as $T_{50}$(70° C.@20 mA/cm²), which is projected longer than 400 hours. The normalized luminance vs. operational time and the drive voltage vs. operational time, tested at 70° C. and at 20 mA/cm², are shown in FIGS. 3 and 4, respectively.

TABLE 1

| Example (EL measured @ RT and 20 mA/cm²) | Voltage (V) | Luminance (cd/m²) | Luminous Efficiency (cd/A) | CIE x (1931) | CIE y (1931) | EL Peak (nm) | Power Efficiency (lm/W) | $T_{50}$ (70° C. @20 mA/cm²) (h) |
|---|---|---|---|---|---|---|---|---|
| 4 (Comparative) | 7.3 | 1732 | 8.7 | 0.294 | 0.647 | 524 | 3.8 | ~250 |
| 5 (Comparative) | 7.0 | 1943 | 9.7 | 0.290 | 0.648 | 522 | 4.4 | <2 |
| 6 (Inventive) | 5.0 | 1840 | 9.2 | 0.286 | 0.651 | 522 | 5.8 | >400 |

It is evident, from Table 1, FIGS. 3 and 4, that the OLED having TAPP as an ETL has improved EL performance with lower drive voltage, improved power efficiency, and longer operational lifetime.

The invention has been described in detail with particular reference to certain preferred embodiments thereof, but it will be understood that variations and modifications can be effected within the spirit and scope of the invention.

PARTS LIST

100 OLED
110 substrate
120 anode
130 hole-injecting layer (HIL)
140 hole-transporting layer (HTL)
150 light-emitting layer (LEL)
160 electron-transporting layer (ETL)
170 electron-injecting layer (EIL)
180 cathode
191 electrical conductors
192 voltage/current source
200 OLED

The invention claimed is:

1. An organic compound represented by one of the following formulae:

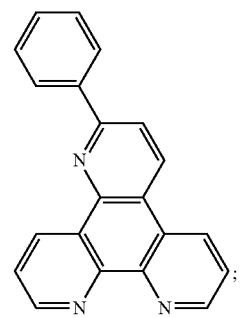

I-1

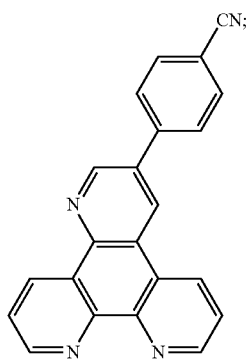
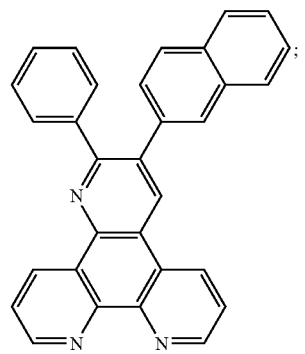
I-2
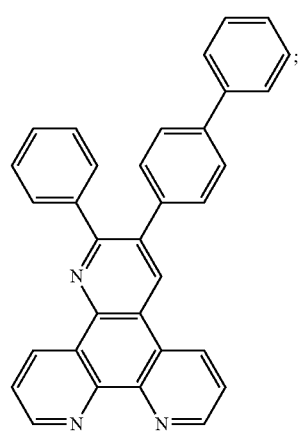
I-3
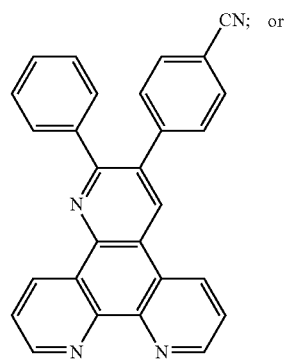
I-4
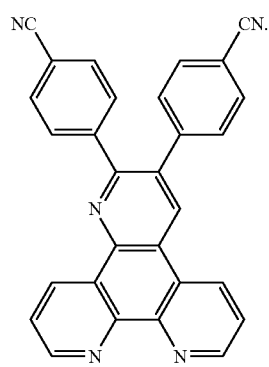
I-5

2. An organic polymer comprising an azatriphenylene structure represented by the formula:

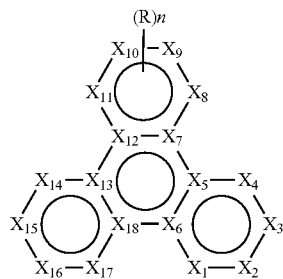

Formula I wherein
X1 to X18 are individually the same or different and where X5-X7, X12-X13 and X18 are all carbon and, where one of X1-X4 is a nitrogen, one of X8-X11 is a nitrogen and one of X14-X17 is a nitrogen, and X1-X4, X8-X11 and X14-X17 other than nitrogen are all carbon;
R is a substituent independently selected from hydrogen, an alkyl group, a cycloalkyl group, a heterocyclic group, an alkenyl group, a cycloalkenyl group, an alkynyl group, a hydroxyl group, a mercapto group, an alkoxy group, an aryl group, a heteroaryl group, an amino group, a cyano group, a nitro group, an alkylthio group, an arylalkyl group, an aryl ether group, an aryl thioether group, a halogen, a haloalkane, a haloalkene, a haloalkyne, a silyl group, a siloxanyl group, an aldehyde group, a carbonyl group, a carboxyl group, an ester group, a carbamoyl group, a sulfonate group, a sulfinate group, an amide group, and a cyclic structure formed with an adjacent substitutent group; and
n is integer of from 1 to 11 and when n is 2 or more the R substituents can form a fused ring structure,
wherein Formula I is part of a repeating unit.

3. An electroluminescent device comprises an anode, a spaced-apart cathode, and at least one electron-transporting layer disposed between the spaced-apart anode and cathode, the electron-transporting layer including a polymer having a structure in accordance with Formula I as a part of a repeating unit:

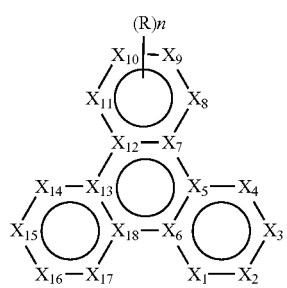

Formula I wherein X1 to X18 are individually the same or different and where X5-X7, X12-X13 and X18 are all carbon and, where one of X1-X4 is a nitrogen, one of X8-X11 is a nitrogen and one of X14-X17 is a nitrogen, and X1-X4, X8-X11 and X14-X17 other than nitrogen are all carbon;
R is a substituent independently selected from hydrogen, an alkyl group, a cycloalkyl group, a heterocyclic group, an alkenyl group, a cycloalkenyl group, an alkynyl group, a hydroxyl group, a mercapto group, an alkoxy group, an aryl group, a heteroaryl group, an amino group, a cyano group, a nitro group, an alkylthio group, an arylalkyl group, an aryl ether group, an aryl thioether group, a halogen, a haloalkane, a haloalkene, a haloalkyne, a silyl group, a siloxanyl group, an aldehyde group, a carbonyl group, a carboxyl group, an ester group, a carbamoyl group, a sulfonate group, a sulfinate group, an amide group, and a cyclic structure formed with an adjacent substitutent group; and
n is integer of from 1 to 11 and when n is 2 or more the R substituents can form a fused ring structure.

4. The electroluminescent device of claim 3 wherein X1 and X17 are nitrogen atoms or X1 and X14 are nitrogen atoms.

5. The electroluminescent device of claim 4 wherein X8 or X11 are nitrogen.

6. An electroluminescent device comprises an anode, a spaced-apart cathode, and at least one electron-transporting layer disposed between the spaced-apart anode and cathode, the electron-transporting layer including a compound represented by one of the following formulae:

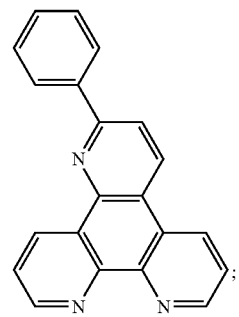

I-1

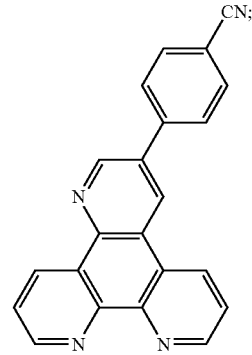

I-2

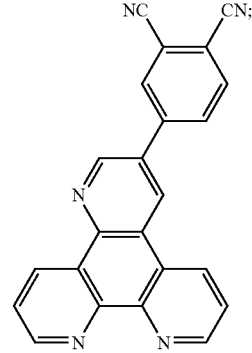

I-3

I-4 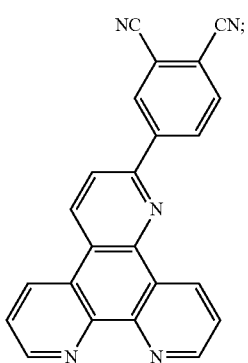

I-5 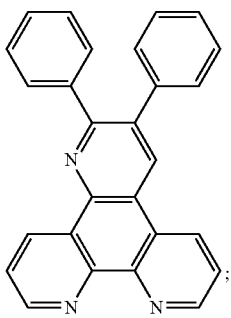

I-6 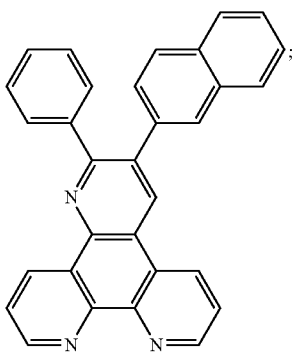

I-7 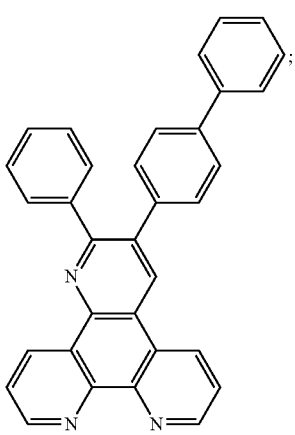

I-8 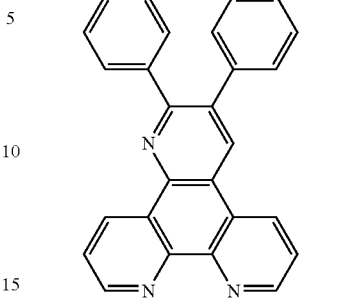 or

I-9 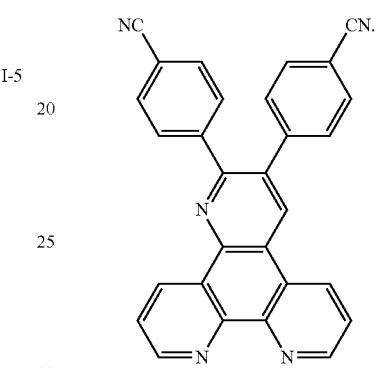

7. The electroluminescent device of claim 3 wherein the electron-transporting layer is doped with at least one dopant having a work function less than 4.0 eV.

8. The electroluminescent device of claim 7 wherein the at least one dopant in the electron-transporting layer includes alkali metals, alkali metal compounds, alkaline earth metals, or alkaline earth metal compounds.

9. The electroluminescent device of claim 7 wherein the at least one dopant in the electron-transporting layer includes Li, Na, K, Rb, Cs, Mg, Ca, Sr, Ba, La, Ce, Nd, Sm, Eu, Tb, Dy, or Yb.

10. A method of making an electroluminescent device, comprising:
   a) providing an anode and a spaced-apart cathode; and
   b) depositing between the anode and spaced-apart cathode at least one electron-transporting layer, which includes a polymer having a structure in accordance with Formula I as a part of a repeating unit:

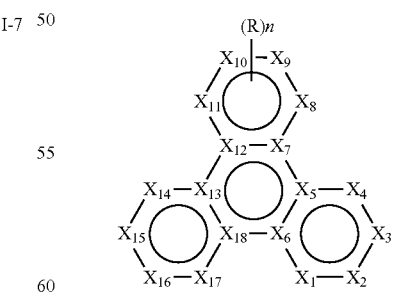

Formula I wherein
X1 to X18 are individually the same or different and where X5-X7, X12-X13 and X18 are all carbon and, where one of X1-X4 is a nitrogen, one of X8-X11 is a nitrogen and one of X14-X17 is a nitrogen, and X1-X4, X8-X11 and X14-X17 other than nitrogen are all carbon;

R is a substituent independently selected from hydrogen, an alkyl group, a cycloalkyl group, a heterocyclic group, an alkenyl group, a cycloalkenyl group, an alkynyl group, a hydroxyl group, a mercapto group, an alkoxy group, an aryl group, a heteroaryl group, an amino group, a cyano group, a nitro group, an alkylthio group, an arylalkyl group, an aryl ether group, an aryl thioether group, a halogen, a haloalkane, a haloalkene, a haloalkyne, a silyl group, a siloxanyl group, an aldehyde group, a carbonyl group, a carboxyl group, an ester group, a carbamoyl group, a sulfonate group, a sulfinate group, an amide group, and a cyclic structure formed with an adjacent substitutent group; and n is integer of from 1 to 11 and when n is 2 or more the R substituents can form a fused ring structure.

11. An organic material for use in an electronic device wherein the material is a polymer having a structure in accordance with Formula I as a part of a repeating unit:

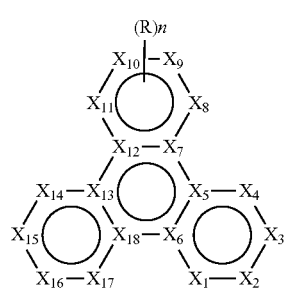

Formula I wherein

X1 to X18 are individually the same or different and where X5-X7, X12-X13 and X18 are all carbon and, where one of X1-X4 is a nitrogen, one of X8-X11 is a nitrogen and one of X14-X17 is a nitrogen, and X1-X4, X8-X11 and X14-X17 other than nitrogen are all carbon;

R is a substituent independently selected from hydrogen, an alkyl group, a cycloalkyl group, a heterocyclic group, an alkenyl group, a cycloalkenyl group, an alkynyl group, a hydroxyl group, a mercapto group, an alkoxy group, an aryl group, a heteroaryl group, an amino group, a cyano group, a nitro group, an alkylthio group, an arylalkyl group, an aryl ether group, an aryl thioether group, a halogen, a haloalkane, a haloalkene, a haloalkyne, a silyl group, a siloxanyl group, an aldehyde group, a carbonyl group, a carboxyl group, an ester group, a carbamoyl group, a sulfonate group, a sulfinate group, an amide group, and a cyclic structure formed with an adjacent substitutent group; and n is integer of from 1 to 11 and when n is 2 or more the R substituents can form a fused ring structure.

* * * * *